(12) United States Patent
Kim

(10) Patent No.: US 12,194,286 B2
(45) Date of Patent: Jan. 14, 2025

(54) FILTER-INTEGRATED MEDICINE TRANSFER DEVICE AND MEDICINAL LIQUID INJECTION APPARATUS INCLUDING THE SAME

(71) Applicant: Yong Hyun Kim, Gyeonggi-do (KR)

(72) Inventor: Yong Hyun Kim, Gyeonggi-do (KR)

( * ) Notice: Subject to any disclaimer, the term of this patent is extended or adjusted under 35 U.S.C. 154(b) by 842 days.

(21) Appl. No.: 17/283,362

(22) PCT Filed: Oct. 18, 2019

(86) PCT No.: PCT/KR2019/013766
§ 371 (c)(1),
(2) Date: Apr. 7, 2021

(87) PCT Pub. No.: WO2020/080893
PCT Pub. Date: Apr. 23, 2020

(65) Prior Publication Data
US 2021/0379298 A1    Dec. 9, 2021

(30) Foreign Application Priority Data

Oct. 19, 2018 (KR) .................. 10-2018-0125465
Nov. 7, 2018 (KR) .................. 10-2018-0136152
Dec. 11, 2018 (KR) .................. 10-2018-0159283

(51) Int. Cl.
*A61M 5/38* (2006.01)
*A61J 1/20* (2006.01)
(Continued)

(52) U.S. Cl.
CPC ............ *A61M 5/385* (2013.01); *A61J 1/2082* (2015.05); *A61M 5/141* (2013.01); *A61M 5/165* (2013.01);
(Continued)

(58) Field of Classification Search
CPC ...... A61M 5/385; A61M 5/141; A61M 5/165; A61M 2005/1402; A61M 5/16804; A61J 1/2082
See application file for complete search history.

(56) References Cited

U.S. PATENT DOCUMENTS

| 4,515,606 A | 5/1985 | de Winter |
| 4,571,244 A * | 2/1986 | Knighton ........... B01D 19/0031 604/126 |

(Continued)

FOREIGN PATENT DOCUMENTS

| CN | 102365107 A | 2/2012 |
| CN | 102716533 A | 10/2012 |

(Continued)

*Primary Examiner* — Courtney B Fredrickson
(74) *Attorney, Agent, or Firm* — Clark Hill PLC; James R. Foley

(57) ABSTRACT

A channel for a medicinal liquid is formed in a filter-integrated medicine transfer device according to an embodiment of the present disclosure. The filter-integrated medicine transfer device includes: a housing having an air passage that diverges from a medicinal liquid channel and is connected to outside; at least one hydrophobic air-passing filter disposed in the housing and disposed at a boundary between the air passage and the medicinal liquid channel; and at least one medicine transfer pipe disposed in the housing and having a capillary channel constituting a portion of the medicinal liquid channel.

14 Claims, 18 Drawing Sheets

(51) Int. Cl.
*A61M 5/14* (2006.01)
*A61M 5/165* (2006.01)

(52) U.S. Cl.
CPC ....... *A61M 5/38* (2013.01); *A61M 2005/1402* (2013.01); *A61M 2005/1652* (2013.01); *A61M 2005/1657* (2013.01); *A61M 2205/7536* (2013.01)

(56) References Cited

U.S. PATENT DOCUMENTS

| | | | |
|---|---|---|---|
| 4,828,587 | A | 5/1989 | Baurmeister et al. |
| 5,290,238 | A | 3/1994 | Crass et al. |
| 2005/0245871 | A1 | 11/2005 | Delnevo et al. |
| 2011/0106048 | A1 | 5/2011 | Walborn |
| 2011/0132482 | A1 | 6/2011 | Honma et al. |
| 2012/0022449 | A1* | 1/2012 | Kim ............ A61M 5/385 604/126 |
| 2012/0234757 | A1* | 9/2012 | Martin ............ A61M 5/38 210/95 |
| 2013/0060226 | A1* | 3/2013 | Fini ............ A61M 5/162 604/247 |

FOREIGN PATENT DOCUMENTS

| | | |
|---|---|---|
| CN | 102883762 A | 1/2013 |
| EP | 0254100 A2 | 1/1988 |
| EP | 2500051 A1 | 9/2012 |
| JP | S57-167705 A | 10/1982 |
| JP | H06-39034 A | 2/1994 |
| JP | H09-502127 A | 3/1997 |
| JP | 2001-276181 A | 10/2001 |
| JP | 2005-532105 A | 10/2005 |
| JP | 2012-517275 A | 8/2012 |
| JP | 2012-192178 A | 10/2012 |
| JP | 5265680 B2 | 8/2013 |
| KR | 10-1134279 B1 | 4/2012 |
| KR | 10-2015-0029283 A | 3/2015 |
| KR | 10-1535350 B1 | 7/2015 |
| WO | 95/06506 A1 | 3/1995 |
| WO | 2015/037832 A1 | 3/2015 |

\* cited by examiner

FILTER-INTEGRATED MEDICINE TRANSFER DEVICE AND MEDICINAL LIQUID INJECTION APPARATUS INCLUDING THE SAME

TECHNICAL FIELD

The present disclosure relates to a medicine transfer device for medial liquid injection and a filter for filtering out air in a medicinal liquid.

BACKGROUND ART

A medicinal liquid injection apparatus that injects a liquid-state medicinal liquid (e.g., an injection) into a patient to supply medicine to the patients is known. A medicinal liquid that is in a predetermined storage space is injected into the body of a patient through a channel (e.g., the internal space of a tube and a needle) connected to the patient by the medicinal liquid injection apparatus.

A device having a medicinal liquid transfer pipe forming a capillary channel to prevent a medicinal liquid from being injected all at once into the body of a patient such that the medicinal liquid is slowly injected for a predetermined time for medical purposes is known. Since a medicinal liquid flows through the medicine transfer pipe, the flow rate of the medicinal liquid flowing through the channel of the medicinal liquid injection apparatus is reduced.

When the storage space is filled with a medicinal liquid, air may flow inside together with the medicinal liquid and move through the passage. Further, substances dissolved in the medicinal liquid (e.g., dissolve oxygen or dissolved carbon dioxide) may change into air and move through the passage, depending on conditions such as pressure in the passage.

DISCLOSURE OF INVENTION

Technical Problem

Air moving through a passage may have a critical adverse influence on a patient when it flows into the patient's body. Further, when air moving through a passage clogs a medicine transfer pipe, the medicine transfer pipe has difficulty in performing its normal function. Embodiments of the present disclosure solve the problems in the related art.

Since the medicinal liquid transfer pipe has a capillary channel having a very small channel cross-sectional area, a loss of head depending on a channel length is large in the medicinal liquid transfer pipe and a pressure drop due to the loss of head makes substances dissolved in a medicinal liquid (e.g., dissolved oxygen or dissolved carbon dioxide) be easily discharged out of the medicinal liquid. There is a problem in that when air produced in a medicinal liquid transfer pipe flows into the body of a patient, the air may cause a critical adverse influence to the patient. Embodiments of the present disclosure solve the problems in the related art.

There is a problem in that even though air is filtered out by an air-passing filter, substances dissolved in a medicinal liquid may change into air at a downstream position of the air-passing filter and may flow into the body of a patient or clog a medicine transfer pipe. Embodiments of the present disclosure solve the problems in the related art.

Solution to Problem

An aspect of the present disclosure provides embodiments of a filter-integrated medicine transfer device. A medicinal liquid channel is formed in a filter-integrated medicine transfer device according to a representative embodiment. The filter-integrated medicine transfer device includes: a housing having an air passage that diverges from the medicinal liquid channel and is connected to outside; at least one hydrophobic air-passing filter disposed in the housing and disposed at a boundary between the air passage and the medicinal liquid channel; and at least one medicine transfer pipe disposed in the housing and having a capillary channel constituting a portion of the medicinal liquid channel.

In an embodiment, the air-passing filter may be configured to pass air in a first direction that is any one direction crossing an extension direction of the capillary channel.

In an embodiment, the housing may have a vent hole positioned at a position where the air passage is connected to an external space, and being open in the first direction.

In an embodiment, the housing may include: a medicine transfer pipe housing to which the medicine transfer pipe is coupled; and a filter housing to which the air-passing filter is coupled. The medicinal liquid channel may include a filtering channel formed in the filter housing. The filtering channel may have at least one curved or bent portion.

In an embodiment, the at least one curved or bent portion may be curved or bent in a first direction crossing an extension direction of the capillary channel.

In an embodiment, the medicinal liquid channel may include a contact channel configured such that a medicinal liquid in the contact channel comes in contact with the air-passing filter. The contact channel may be positioned at an upstream side or a downstream side of the capillary channel.

In an embodiment, the contact channel may be positioned at an upstream side of the capillary channel such that the medicinal liquid that has passed through the contact channel flows into the capillary channel.

In an embodiment, the contact channel may be positioned at a downstream side of the capillary channel such that the medicinal liquid that has passed through the capillary channel flows into the contact channel.

In an embodiment, the at least one medicine transfer pipe may include: a first medicine transfer pipe having a first capillary channel constituting a portion of the medicinal liquid channel; and a second medicine transfer pipe having a second capillary channel disposed at a downstream side of the first capillary channel such that a medicinal liquid that has passed through the first capillary channel flows into the second capillary channel.

In an embodiment, the medicinal liquid channel may include a contact channel configured such that the medicinal liquid in the contact channel comes in contact with the air-passing filter. The contact channel may be positioned at a downstream side of the first capillary channel and at an upstream side of the second capillary channel.

In an embodiment, the filter-integrated medicine transfer device may further comprise a hydrophilic boundary filter disposed at a boundary between a first channel at an upstream side in the medicinal liquid channel and a second channel at a downstream side in the medicinal liquid channel. The air-passing filter may be disposed at a boundary between the air passage and the first channel.

In an embodiment, the capillary channel may be positioned at a downstream side of the second channel.

In an embodiment, the filter-integrated medicine transfer device may further comprise an intake filter disposed at an upstream side of the capillary channel and a downstream side of the boundary filter to pass a medicinal liquid.

In an embodiment, the filter-integrated medicine transfer device may further comprise an additional hydrophobic air-passing filter disposed in the air passage and configured to pass air that has passed through the air-passing filter.

Another aspect of the present disclosure provides embodiments of a medicinal liquid injection apparatus. A medicinal liquid injection apparatus according to a representative embodiment includes: a pumping device configured to press a medicinal liquid; an extension tube in which the medicinal liquid flowing out of the pumping device by pressure applied by the pumping device flows; and a filter-integrated medicine transfer device connected to the extension tube and having a medicinal liquid channel. The filter-integrated medicine transfer device includes: a housing having an air passage that diverges from the medicinal liquid channel and is connected to outside; at least one hydrophobic air-passing filter disposed in the housing and disposed at a boundary between the air passage and the medicinal liquid channel; and at least one medicine transfer pipe disposed in the housing and having a capillary channel constituting a portion of the medicinal liquid channel.

Advantageous Effects of Invention

According to an embodiment of the present disclosure, by conveniently filtering out air flowing inside together with a medicinal liquid or air produced from a medicinal liquid, it is possible to prevent air from being injected into a human body and prevent a medicine transfer pipe from being clogged with air.

According to embodiments of the present disclosure, the possibility of air being produced from the medicinal liquid at the downstream side of the air-passing filter is remarkably reduced, so it is possible to decrease the possibility of air flowing into the medicine transfer pipe disposed at a downstream side of the air-passing filter.

According to embodiments of the present disclosure, it is possible to easily discharge the air passing through the medicine transfer pipe or air produced in the medicine transfer pipe to the outside.

According to embodiments of the present disclosure, it is possible to prevent production of air from a medicinal liquid passing through the medicine transfer pipe or to considerably reduce the amount of air that is produced.

According to embodiments of the present disclosure, by filtering out impurities other than air in a medicinal liquid, it is possible to prevent impurities from being injected into a human body and to prevent the medicine transfer pipe from being clogged with impurities.

MODE FOR THE INVENTION

Embodiments of the present disclosure are illustrated for the purpose of explaining the technical idea of the present disclosure. The scope of the rights according to the present disclosure is not limited to the embodiments presented below or the detailed descriptions of such embodiments.

All technical and scientific terms used in the present disclosure have the meaning generally understood by those of ordinary skill in the art to which the present disclosure pertains, unless otherwise defined. All terms used in the present disclosure are chosen for the purpose of more clearly describing the present disclosure and are not chosen to limit the scope of rights according to the present disclosure.

As used in the present disclosure, expressions such as "comprising", "including", "having", and the like are to be understood as open-ended terms having the possibility of encompassing other embodiments, unless otherwise mentioned in the phrase or sentence containing such expressions.

The singular form described in the present disclosure may include a plural meaning, unless otherwise mentioned. This applies equally to the singular form recited in the claims.

The expressions, such as "first," "second," etc., which are shown in various embodiments of the present disclosure, are used to separate a plurality of elements from each other, and are not intended to limit an order or importance of the corresponding elements.

In the present disclosure, the description that one element is "connected," or "coupled" to another element should be appreciated to indicate that one element may be directly connected, or coupled, to another element, and should be further understood that a new element may be interposed between one element and another element.

Figure 5:
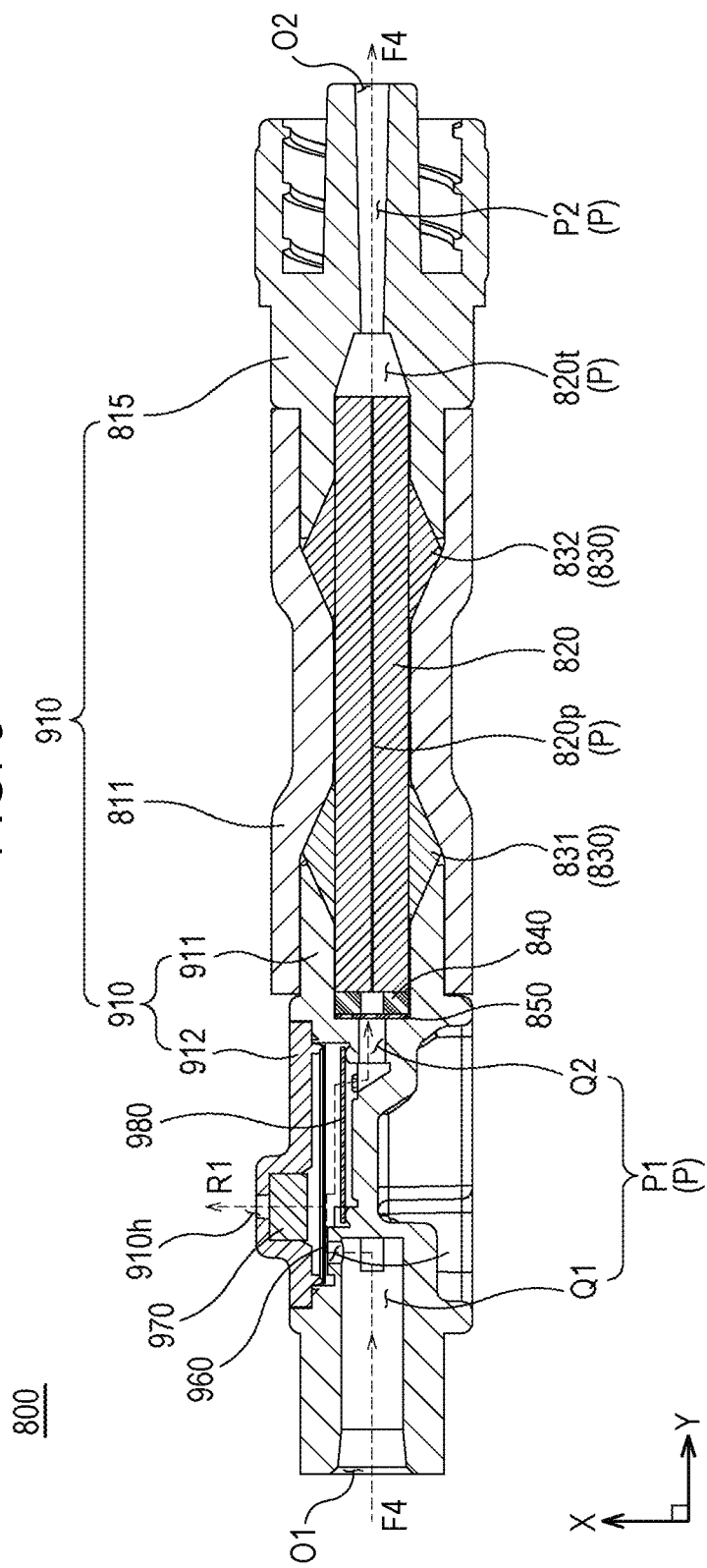
FIG. 5 is a vertical cross-sectional view of the medicine transfer device 800 of FIG. 2.

Terms "upstream" and "downstream" used herein are defined on the basis of the flow direction of a medicinal liquid when a pumping device 100 presses the medicinal liquid. In detail, the directions of the arrows F2 and F3 in FIGS. 1 and F4 in FIG. 5 are defined as downstream directions and the direction opposite to the downstream direction is defined as an upstream direction.

It should be understood that the term "medicinal liquid" used herein includes not only liquid containing treatment substances, but liquid that assists treatment substances or can be used with treatment substances and liquid that can be injected into a patient. Priming liquid to be described below is a kind of those medicinal liquids.

Hereafter, embodiments of the present disclosure are described with reference to the accompanying drawings. The same or corresponding components may be given the same reference numerals in the accompanying drawings. Further, repeated description of the same or corresponding components may be omitted in the following description of the embodiments. However, omission of a description of components is not intended to mean exclusion of the components from the embodiments.

Figure 1:
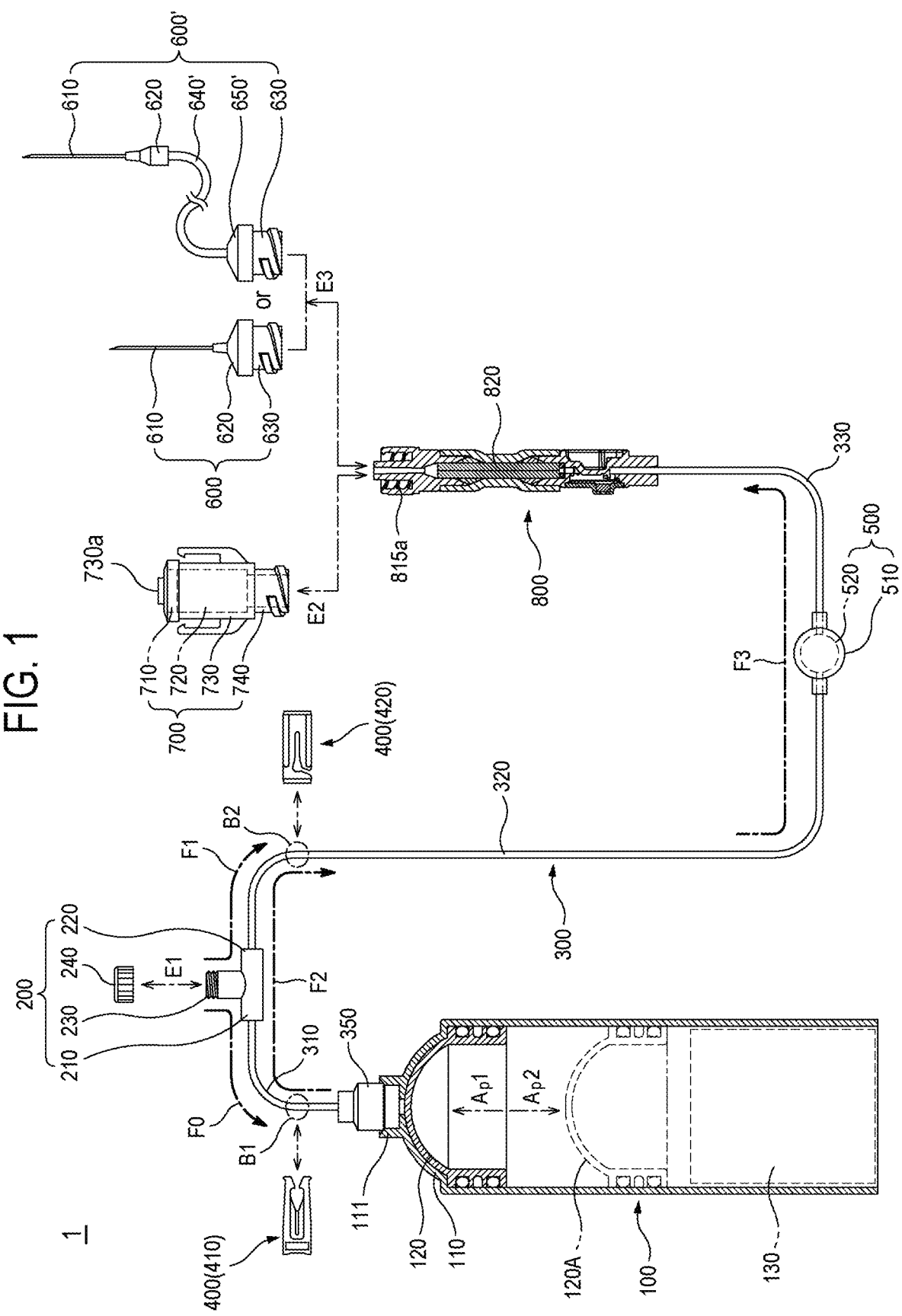
FIG. 1 is a conceptual diagram of the entire system of a medicinal liquid injection apparatus 1 according to an embodiment.

FIG. 1 is a conceptual diagram of the entire system of a medicinal liquid injection apparatus 1 according to an embodiment. A process of injecting a medicinal liquid into a patient using the medicinal liquid injection apparatus 1 according to embodiments of the present disclosure includes a priming step and a medicinal liquid injection step that are sequentially performed.

Referring to FIG. 1, in the priming step, a priming liquid is made to flow through an extension tube 300. The priming liquid flowing through the extension tube 300 flows into the filter-integrated medicine transfer device 800. The medicinal liquid injection apparatus 1 may include an end cap 700 separably connected to the downstream side of the medicine transfer device 800. Air in the extension tube 300 can be discharged outside through the end cap 700.

Accordingly, the extension tube 300 and the medicine transfer device 800 are filled with the priming liquid. The priming liquid may be a liquid that contains treatment substances or that can be injected into a patient such as a saline solution.

The end cap 700 is configured to receive air and the priming liquid flowing through the medicine transfer device 800. The end cap 700 may be configured to allow air to flow outside, but to prevent the priming liquid from flowing outside.

The end cap 700 includes a vent filter 710 that blocks the priming liquid, but passes gas. The vent filter 710 includes a hydrophobic filter. The end cap 700 may include a sponge 720 disposed at an upstream side of the vent filter 710. The end cap 700 includes an end cap casing 730 accommodating the vent filter 710 therein. The end cap casing 730 accommodates the sponge 720 therein. The end cap casing 730 has a vent hole 730a through which gas passes. The end cap 700 includes an end cap coupling portion 740 configured to be coupled to a downstream connecting portion 815a of the medicine transfer device 800. The arrow E2 in FIG. 1 indicates the direction in which the end cap coupling portion 740 is coupled to and separated from the downstream connecting portion 815a.

When the end cap 700 is filled with the priming liquid, it is possible to separate the end cap 700 from the medicine transfer device 800 and then connect a patient connector 600 or 600' to the medicine transfer device 800.

The patient connector 600 or 600' may include a needle 610 or a catheter. The patient connector 600 or 600' includes a component that is injected into the body of a patient such as the needle 610.

The patient connector 600 or 600' may include 'an insert part including a component that is injected into the body of a patient such as the needle 610' and 'the other part'. The insert part and the other part may be configured to be separable from each other. In this case, with the insert part connected to a patient but separated from the other part, a user can couple the other part to the medicine transfer device 800 and then combine the insert part and the other part with each other. In this case, the liquid that has passed through the medicine transfer device 800 can flow into the body of the patient sequentially through the other part and the insert part.

The patient connector 600 or 600' includes a needle supporting portion 620 that supports the needle 610. The patient connector 600 or 600' includes a unit coupling portion 630 configured to be coupled to the downstream connecting portion 815a of the medicine transfer device 800. The arrow E3 in FIG. 1 indicates the direction in which the unit coupling portion 630 is coupled to and decoupled from the downstream connecting portion 815a.

For example, the patient connector 600 can be formed by sequentially connecting the needle 610, the needle supporting portion 620, and the unit coupling portion 630.

As another example, the patient connector 600 further has a patient connection tube fixing portion 650' connected to the downstream side of the unit coupling portion 630. The patient connector 600' further includes a patient connection tube 640' connecting the patient connection tube fixing portion 650' and the needle supporting portion 620. The patient connection tube 640' may be made of a flexible material. The patient connector 600' can be formed by sequentially connecting the needle 610, the needle supporting portion 620, the patient connection tube 640', the patient connection tube fixing portion 650', and the unit coupling portion 630.

In the medicinal liquid injection step, medicinal liquid is injected into the body of a patient by pressure that is applied by a pumping device 100. In the medicinal liquid injection step, the medicinal liquid is a liquid containing treatment substance. When the priming liquid is not a liquid containing treatment substance, but a saline solution, etc., the priming liquid can be injected first into the body of a patient and the liquid containing treatment substance flowing behind the priming liquid can be injected into the body of the patient.

The pumping device 100 includes a chamber 110 configured to be able to accommodate a medicinal liquid. The chamber 110 forms an internal space in cooperation with a pressing part 120. A medicinal liquid can be stored in the internal space. In another embodiment, a saline solution, etc. can be temporarily stored in the internal space. A discharge port 111 through which the liquid in the chamber 110 is discharged is formed at the chamber 110.

The pumping device 100 is configured to press a medicinal liquid. The pumping device 100 includes the pressing part 120 that presses the liquid in the chamber 110. The pressing part 120 can press the liquid in the chamber 110 by moving in a predetermined pressing direction Ap1. When a liquid is supplied into the chamber 110, the pressing part 120 is moved in the opposite direction Ap2 to the pressing direction Ap1. In FIG. 1, the position of the pressing part 120 that has moved in the opposite direction Ap2 is shown with reference to 120A.

The pumping device 100 may include a pressure operation part 130 that provides power such that the pressing part 120 moves in the pressing direction Ap1. For example, the pressure operation part 130 may be configured to press the liquid in the chamber 110 using volume expansion due to gas activation. As another example, the pressure operation part 130 provides a portion that a user can hold, so the user can move the pressing part 120 in the pressing direction Ap1 by applying force.

Though not shown, as another example, the pressing part 120 may be configured to press a liquid using the elasticity of an elastic member such as a balloon. In this case, the pressing part 120 may include the balloon configured to press a liquid in the balloon.

A medicinal liquid injection valve 200 is configured to fill the chamber 110 with a liquid. A liquid can flow into the extension tube 300 or the chamber 110 through the medicinal liquid injection valve 200. The medicinal liquid injection valve 200 may be connected to the extension tube 300 or, in another embodiment not shown in the figures, the medicinal liquid injection valve 200 may be connected to the chamber 110.

The medicinal liquid injection valve 200 has a first extension 210 connected to the downstream end of the first connecting portion 310 of the extension tube 300 and a second extension 220 connected to the upstream end of the second connecting portion 320 of the extension tube 300. The medicinal liquid injection valve 200 has an intake portion 230 configured such that a liquid can flow inside from the outside, and an intake port opening/closing part 240 that is separably coupled to the intake portion 230. The arrow E1 in FIG. 1 indicates the directions in which the intake port opening/closing part 240 is coupled and decoupled from the intake portion 230.

The extension tube 300 is configured to guide the flow of the priming liquid. The extension tube 300 can guide a medicinal liquid from the pumping device 100 to the medicine transfer device 800.

The extension tube 300 is configured such that a medicinal liquid discharged from the pumping device 100 by pressure applied by the pumping device 100 flows in the extension tube 300. The upstream end of the extension tube 300 is connected to the pumping device 100. The extension tube 300 has an upstream connecting portion 350 connected to a medicinal liquid injection discharge port 111 of the pumping device 100.

The downstream end of the extension tube 300 is connected to the medicine transfer device 800. A liquid that has passed through the extension tube 300 flows into the medicine transfer device 800 through the intake port of the medicine transfer device 800.

The extension tube 300 has a first connecting portion 310 connecting the upstream connecting portion 350 and the first extension 210 of the medicinal liquid injection valve 200. The extension tube 300 has a second connecting portion 320 connecting the second extension 220 of the medicinal liquid injection valve 200 and an external filter device 500. The extension tube 300 has a third connecting portion 330 connecting the external filter device 500 and the downstream end of the extension tube 300.

The medicinal liquid injection apparatus 1 may include at least one connection tube opening/closing device 400. The connection tube opening/closing device 400 can block the flow of a liquid at a predetermined point of the extension tube 300 by pressing the outer side of the extension tube 300. The at least one connection tube opening/closing device 400 may include a first opening/closing device 410 that can change whether to open/close a point B1 of the first connecting portion 310 and a second opening/closing device 420 that can change whether to open/close a portion B2 of the second connecting portion 320. For example, the connection tube opening/closing device 400 may be configured to be in a clamp shape.

The medicinal liquid injection apparatus 1 may include the external filter device 500 disposed on the extension tube 300. The external filter device 500 may include a filter casing 510 connected with the extension tube 300 and a filter 520 disposed in the filter casing 510. A particle filter that filters out impurities, an air filter that filters out air bubbles, or a combination thereof may be used as the filter 520 of the external filter device 500. The external filter device 500 may have an air vent configured such that the air filtered through the air filter is discharged outside.

The priming step and the medicinal liquid injection step according to one embodiment are described hereafter. In the priming step according to the one embodiment, not a medicinal liquid, but a saline solution, etc. is used as the priming liquid. In the priming step according to the one embodiment, the intake port opening/closing part 240 is separated from the inlet 230, the first connecting portion 310 is closed by the first connection tube opening/closing device 410 (see B1), and the other portion of the extension tube 300 except for the first connecting portion 310 is opened. Referring to the arrows F1 and F3, the priming liquid such as a saline solution, etc. flows sequentially through the inlet 230, the second extension 220, the second connecting portion 320, the third connecting portion 330, and the medicine transfer device 800, whereby the extension tube 300 and the medicine transfer device 800 are filled with the priming liquid.

After the priming step according to the one embodiment, the medicinal liquid injection step according to the one embodiment is performed. In the medicinal liquid injection step according to the one embodiment, the intake port opening/closing part 240 is separated from the inlet 230, the second connecting portion 320 is closed by the second connection tube opening/closing device 420 (see B2), and the first connecting portion 310 is opened by separating the first connection tube opening/closing device 410 from the first connecting portion 310. Referring to the arrow F0, while a medicinal liquid flows into the chamber 110 through the medicinal liquid injection valve 200 and the first connecting portion 310, the pressing part 120 is moved in the direction Ap2. Thereafter, the intake port opening/closing part 240 is coupled to the inlet 230 and the second connection tube opening/closing device 420 is separated from the second connecting portion 320, thereby opening the extension tube 300. Referring to the arrows F2 and F3, thereafter, the pressing part 120 is moved in the pressing direction Ap1, so the medicinal liquid can sequentially pass through the extension tube 300 and the medicine transfer device 800.

A priming step and a medicinal liquid injection step according to a different embodiment are described hereafter. In the priming step according to the different embodiment, a medicinal liquid is used as the priming liquid. In the priming step according to the different embodiment, the chamber 110 is filled with a medicinal liquid, the end cap 700 is connected to the medicine transfer device 800, the inlet 230 is closed by the intake port opening/closing part 240, and the connection tube opening/closing device 400 is separated from the extension tube 300, thereby opening the extension tube 300. Referring to the arrows F2 and F3, thereafter, the pressing part 120 is moved in the pressing direction Ap1, so the medicinal liquid that is the priming medicinal liquid can sequentially pass through the extension tube 300 and the medicine transfer device 800. Accordingly, the extension tube 300 and the medicine transfer device 800 are filled with the priming liquid.

After the priming step according to the different embodiment, the medicinal liquid injection step according to the different embodiment is performed. In the medicinal liquid injection step according to the different embodiment, referring to the arrows F2 and F3, the pressing part 120 is further moved in the pressing direction Ap1, so the medicinal liquid can sequentially pass through the extension tube 300 and the medicine transfer device 800.

Figure 2:
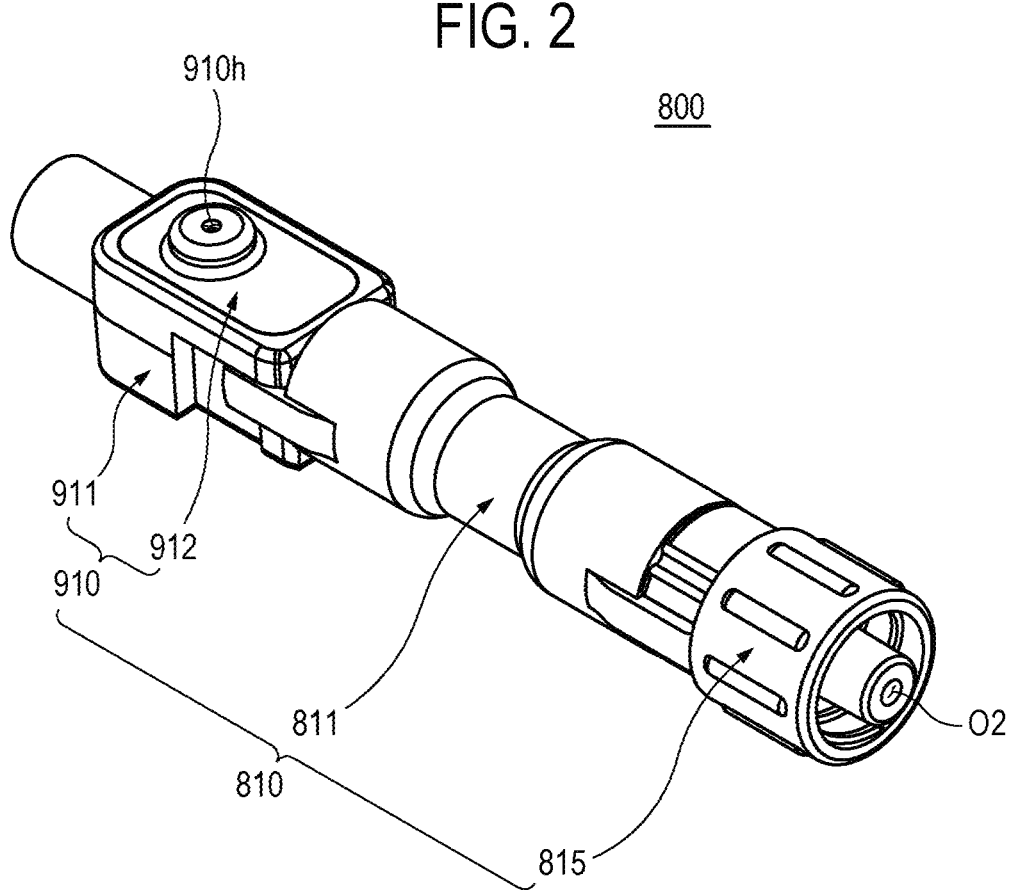
FIG. 2 is a perspective view of a filter-integrated medicine transfer device 800 according to a first embodiment.
Figure 3:
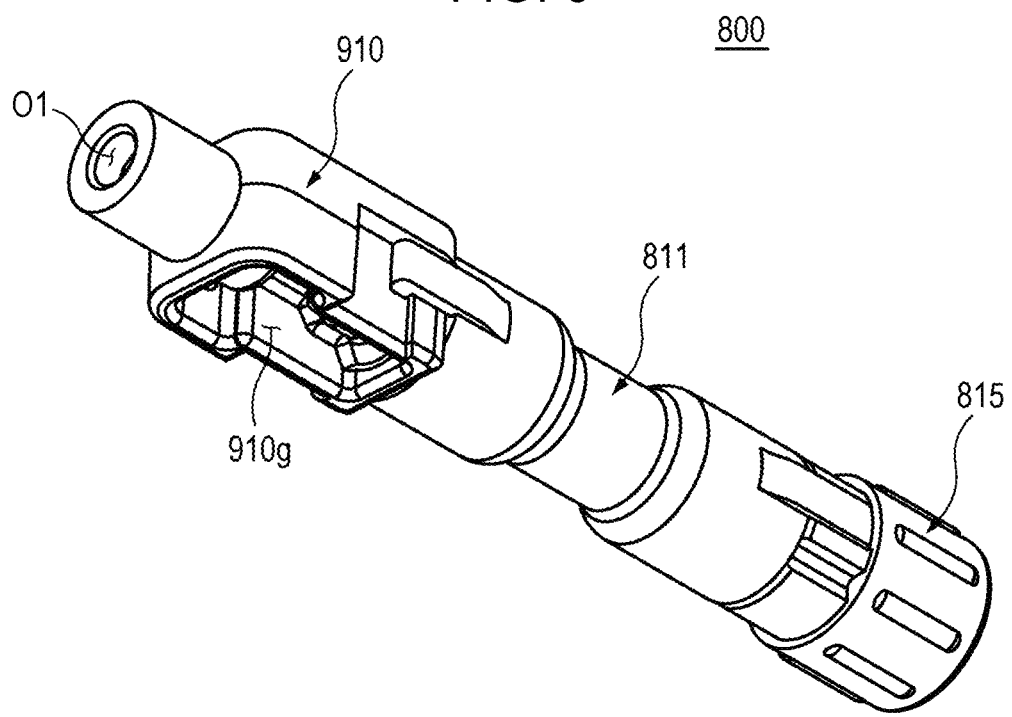
FIG. 3 is a perspective view showing the medicine transfer device 800 of FIG. 2 viewed in another direction.
Figure 4:
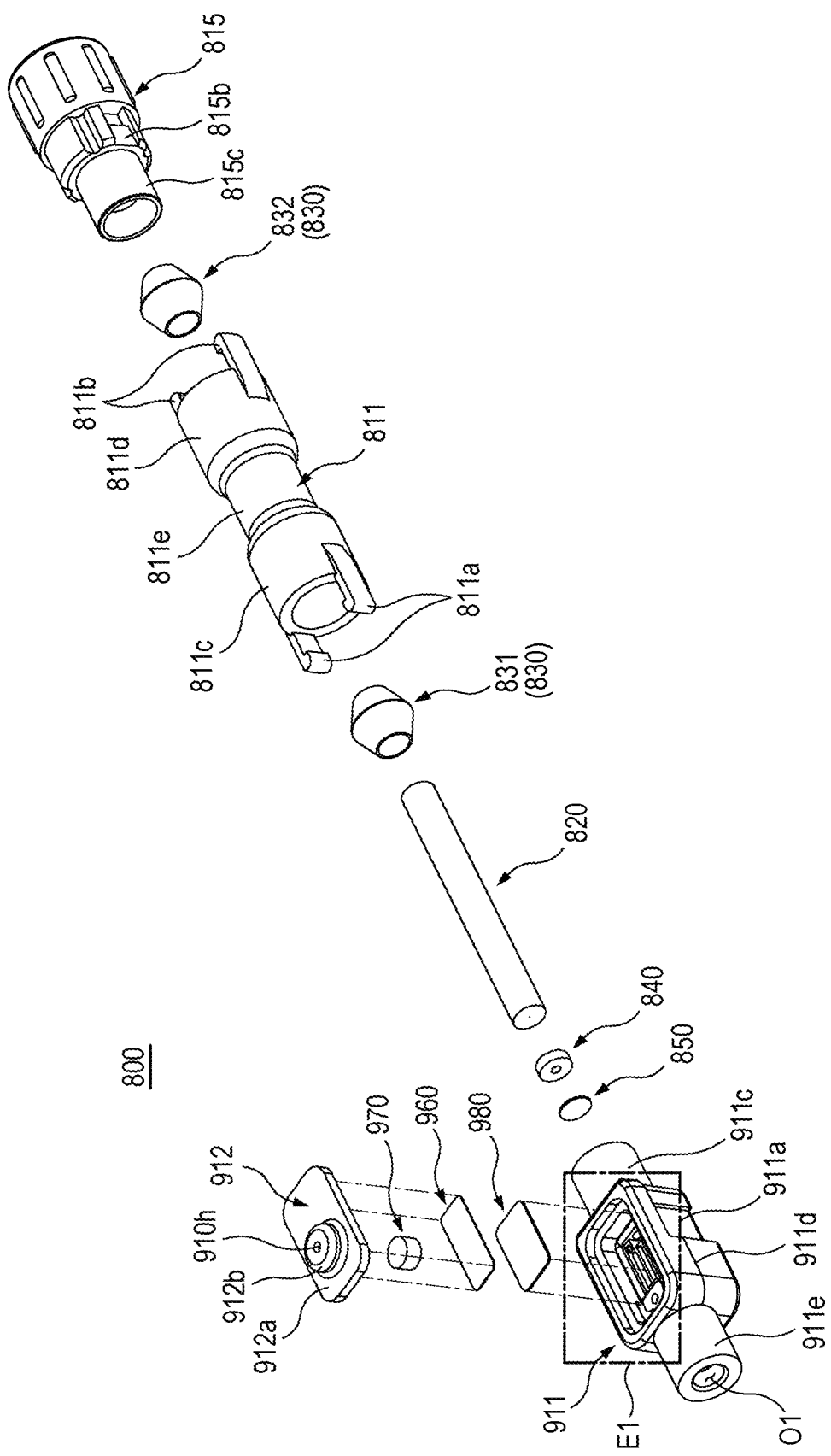
FIG. 4 is an exploded perspective view of the medicine transfer device 800 of FIG. 2.

FIG. 2 is a perspective view of a filter-integrated medicine transfer device 800 according to a first embodiment. FIG. 3 is a perspective view showing the medicine transfer device 800 of FIG. 2 viewed in another direction. FIG. 4 is an exploded perspective view of the medicine transfer device 800 of FIG. 2. FIG. 5 is a vertical cross-sectional view of the medicine transfer device 800 of FIG. 2. The medicine transfer device 800 according to the first embodiment is described hereafter with reference to FIGS. 2 to 5.

The filter-integrated medicine transfer device 800 means a device in which the medicine transfer pipe 820 and the air-passing filter 960 are disposed in one housing 810. In this configuration, the housing 810 may be formed by combining two or more parts or may be constituted by one part.

A medicinal liquid channel P is formed in the medicine transfer device 800. The medicine transfer device 800 is connected to the extension tube 300. An air passage R diverging from the channel P and connected to the outside is formed in the medicine transfer device 800. The medicine transfer device 800 includes at least one hydrophobic air-passing filter 960 disposed at the boundary between the air passage R and the medicinal liquid channel P. The medicine transfer device 800 includes at least one medicine transfer pipe 820 having a capillary channel 820$p$ constituting a portion of the channel P. The capillary channel 820$p$ is configured such that a medicinal liquid flows therein. The medicine transfer device 800 includes a housing 810 in which the air-passing filter 960 and the medicine transfer pipes 820 are disposed.

The medicine transfer pipes 820 may have a function of a flow restricting component. That is, the medicine transfer pipes 820 may have a function of restricting the flow rate of a medicinal liquid flowing through the channel P. For example, the medicine transfer pipes 820 may include a capillary pipe. As another example, the medicine transfer pipes 820 may include a polymeric microtube. Further, the medicine transfer pipes 820 may be made of various materials in various shapes having a capillary channel.

The air-passing filter 960 is coupled to the housing 810. The air-passing filter 960 blocks a medicinal liquid, but passes air. The air-passing filter 960 may be disposed at the boundary between the air passage R and the first channel Q1. The arrow R1 in FIG. 5 indicates the direction in which air flows through the passage R.

The medicine transfer pipe 820 is connected to the housing 810. The medicine transfer pipe 820 is configured to adjust the flow rate of the medicinal liquid in the channel P. For example, the capillary channel 820$p$ has a diameter of about 0.04 to 0.08 mm, thereby restricting the flow rate of a medicinal liquid.

At least a portion of the medical transfer pipe 820 may be in contact with the inner surface of the housing 810. The medical transfer pipe 820 may be disposed through the sealing member 830. An upstream end of the medical transfer pipe 820 is the inlet of the capillary channel 820$p$. The upstream end of the medical transfer pipe 820 may be in contact with the spacer 840.

The channel P of a medicinal liquid is connected to the extension tube 300 such that the medicinal liquid that has passed through the extension tube 300 flows into the channel P. At least a portion of the channel P is formed in a housing 810. An air passage R is formed in the housing 810. The air passage R has a vent hole 910$h$ formed at the housing 810.

The channel P may include an upstream channel P1 disposed at an upstream side of the capillary channel 820$p$ in the channel P. The upstream channel P1 has a channel cross-sectional area larger than a channel cross-sectional area of the capillary channel 820$p$. The housing 810 may form the upstream channel P1.

An intake port O1 of the medicine transfer device 800 is the inlet of the upstream channel P1. The upstream channel P1 can connect an intake port O2 and the capillary channel 820$p$. An intake filter 850 may be disposed in the upstream channel P1. A hole of the spacer 840 to be described below may form a downstream end portion of the upstream channel P1.

The channel P may include a downstream channel P2 disposed at a downstream side of the capillary channel 820$p$ in the channel. The downstream channel P2 has a channel cross-sectional area larger than a channel cross-sectional area of the capillary channel 820$p$. The housing 810 may form the downstream channel P2. A discharge port O2 of the medicine transfer device 800 is the exit of the downstream channel P2.

A discharge port O2 of the medicine transfer device 800 is the exit of the downstream channel P2. The downstream channel P2 can connect the capillary channel 820$p$ and the discharge port O2.

In this embodiment, a downstream space 820$t$ is formed between the capillary channel 820$p$ and the downstream channel P2 in the channel P. The downstream space 820$t$ has a channel cross-sectional area larger than a channel cross-sectional area of the capillary channel 820$p$. The downstream space 820$t$ has a channel cross-sectional area larger than a channel cross-sectional area of the downstream channel P2.

In the channel P, a channel including the portion where the air passage R diverges may be referred to as a "filtering channel". Filtering channels Q1 and Q2 constitute a portion of the medicinal liquid channel P. The filtering channels Q1 and Q2 have a channel cross-sectional area larger than that of the capillary channel 820$p$. The air-passing filter 960 is disposed at the boundary between the filtering channels Q1 and Q2 and the air passage R. The filtering channels Q1 and Q2 are the upstream channel P1 in the embodiment, but the filtering channels Q1 and Q2 may be the downstream channel P2 or may be the intervention space 820$s$ in other embodiments.

The filtering channels Q1 and Q2 and the capillary channel 820$s$ may be connected to each other in the medicinal liquid channel P of the medicine transfer device 800. The filtering channels Q1 and Q2 and the capillary channel 820$p$ are sequentially positioned in the channel P in the embodiment, but the sequence may be changed in other embodiments to be described above. In the embodiment, the upstream channel P1, the capillary channel 820$p$, and the downstream channel p2 are sequentially positioned in the channel P.

The medicine transfer device 800 includes a hydrophilic boundary filter 980 disposed in the medicinal liquid channel P. The boundary filter 980 is disposed at the boundary between a first channel Q1 at the upstream side and a second channel Q2 at the downstream side in the channel P. The boundary filter 980 is configured to act as a pressure interface between the first channel Q1 and the second channel Q2 when it is wetted with a medicinal liquid. The first channel Q1 and the second channel Q2 can have different pressures by the boundary filter 980. For example, the boundary filter 980 may be configured in any one manner of a net structure and a fiber structure. The boundary filter 980 may additionally have a function that filters out impurities.

The medicine transfer device 800 may further include a hydrophobic secondary air-passing filter 970. The secondary air-passing filter 970 is disposed in the air passage R such that air that has passed through the air-passing filter 960 passes it. The secondary air-passing filter 970 can perform a function that prevents a medicinal liquid from flowing outside from the inside even if the air holes or the bonding portion of the air-passing filter 960 are damaged. The secondary air-passing filter 970 may be referred to as an additional hydrophobic air-passing filter 970.

The secondary air-passing filter 970 may be made of the same material as the air-passing filter 960 or may be formed by machining a porous plastic material. For example, the secondary air-passing filter 970 may be formed by machining hydrophobic porous plastic resin material in a shape corresponding to the secondary air-passing filter seat 914 on the air passage R. For example, the material of the secondary air-passing filter 970 can be obtained from Porex Corporation (website: www.porex.com) at GA 30213, Fairburn of Georgia in U.S.A. A product named Porex Hydrophobic Vents by Porex Corporation can be used. This product is made of a polyethyle polytetrafluoroethylene material.

An intake port O1 and a discharge port O2 for a medicinal liquid are formed at the housing 810. The medicinal liquid channel P may be formed to connect the intake port O1 and the discharge port O2. The air passage R is formed to connect the middle portion of the channel P to the external space. The air passage R may extend in a first direction X from the middle portion of the channel P. The term "first direction X" used herein may be defined as any one direction that crosses the extension direction of the capillary channel 820p.

The housing 810 includes a medicinal liquid transfer pipe housing part 811 to which the medicinal liquid transfer pipe 820 is coupled. The housing 810 includes a filter housing 910 to which the air-passing filter 960 is coupled. The filter housing 910 can be combined with the medicinal liquid transfer pipe housing part 811. The filtering channels Q1 and Q2 are formed at the filter housing 910. The housing 810 may include a downstream housing part 815 in which the downstream channel P2 is formed. The downstream housing part 815 can be coupled to the downstream side portion of the medicinal liquid transfer pipe housing part 811.

The filter housing 910 may include a filter body 911 forming at least a portion of the filtering channels Q1 and Q2. The boundary filter 980 may be disposed at the filter body 911. The filter body 911 includes a body part 911d forming the outer surface. A contact channel Q1c to be described below may be formed in the body part 911d. A vent cap 912 may be coupled in the first direction X of the body part 911d.

The filter body 911 includes an inlet portion 911e forming an inlet such that a medicinal liquid flows into the filtering channels Q1 and Q2. The inlet portion 911e may protrude in the opposite direction to a second direction Y from the body part 911d. The intake port O1 may be formed at the end in the opposite direction to the second direction Y of the inlet portion 911e. The term "second direction Y" used herein may be defined any one direction perpendicular to the first direction X.

The filter body 911 includes an outlet portion 911c forming an outlet such that a medicinal liquid is discharged from the filtering channels Q1 and Q2. The outlet portion 911c may protrude in the second direction Y from the body part 911d. The discharge port O2 may be formed at the end in the second direction Y of the outlet portion 911c. The outlet portion 911c can be inserted the medicinal liquid transfer pipe housing part 811.

The filter body 911 may accommodate at least a portion of the medicine transfer pipe 820. The upstream side portion of the medicine transfer pipe 820 is accommodated in the filter body 911.

A coring groove 910g that is recessed inward and in which the boundary filter 980 is disposed may be formed on the outer surface of the filter body 911. The groove 910g is formed on an opposite side to the first direction X of the outer surface of the filter body 911. The groove 910g may be formed by recessing the outer surface of the filter body 911 in the first direction X.

The filter housing 910 includes the vent cap 912 coupled to the filter body 911. The filter housing 910 has at least one vent hole 910h formed at the position where the air passage R is connected to the external space. The vent hole 910h is formed at the vent cap 912. The vent hole 910h may be open in the first direction X.

The vent cap 912 has a cover portion 912a coupled to the housing 810. The cover portion 912a may cover the air-passing filter 960. The cover portion 912a covers the contact channel Q1c to be described below. The cover portion 912a may be formed in a plate shape having a thickness in the first direction X.

The vent cap 912 may include a vent protrusion 912b protruding outward from the cover portion 912a. The vent protrusion 912b may protrude in the first direction X. The inner surface of the vent protrusion 912b can limit at least a portion of the air passage R. The vent hole 910h may be formed at a protrusive end of the vent protrusion 912b.

The medicine transfer pipe housing 811 may include a first coupling portion 811a coupled to the filter body 911. The first coupling portion 811a may have a hook shape. The first coupling portion 811a may be latched to a first counter-coupling portion 911a of the filter body 911.

The medicine transfer pipe housing 811 may include a second coupling portion 811b coupled to the downstream housing part 815. The second coupling portion 811b may have a hook shape. The second coupling portion 811b may be latched to a second counter-coupling portion 815b of the downstream housing part 815.

The medicine transfer pipe housing 811 may have a first seat 811c in which a portion of the downstream side of the filter body 911 is inserted. The medicine transfer pipe housing 811 may have a second seat 811d in which a portion of the upstream side of the downstream housing part 815 is inserted.

The medicine transfer pipe housing 811 may have an intervention portion 811e disposed between the first seat 811c and the second seat 811d. The medicine transfer pipe 820 is inserted in the intervention portion 811e.

The downstream housing part 815 may accommodate at least a portion of the medicine transfer pipe 820. The downstream side portion of the medicine transfer pipe 820 is accommodated in the downstream housing part 815. The downstream housing part 815 has an insertion portion 815c that is inserted in the medicine transfer pipe housing 811.

The discharge port O2 is formed at the downstream housing part 815. The downstream connecting portion 815a connected with the patient connector is formed at the downstream housing part 815.

Air may exist in the chamber 110 and the extension tube 300. For example, in the priming step, air may remain without being completely removed in the chamber 110 and the extension tube 300. Air flowing in the air-passing filter 960 together with a medicinal liquid can be discharged through the first channel Q1 and the air passage R.

Further, air is dissolved in a medicinal liquid in the chamber 110 of the medicinal liquid injection apparatus 1. For example, an amount of the air that flows inside when the chamber 110 is filled with a medicinal liquid can be dissolved in the medicinal liquid in the chamber 110 under pressure larger than atmospheric pressure. In relation with this, the amount of air dissolved in the medicinal liquid can be inferred from a formula $c_1/p_1 = c_2/p_2$ according to Henry's law. In the formula, $c_1$ and $c_2$ are molar concentration (mol/L) of the air dissolved in the medicinal liquid, and $p_1$ and $p_2$ are partial pressures of the air. $c_1$ and $p_1$ are values in an any one state, and $c_2$ and $p_2$ are values in another one state.

Since the first channel Q1 is connected with the air passage R, the first channel Q1 has internal pressure relatively low and close to the atmospheric pressure and the second channel Q2 may have internal pressure higher than that of the first channel Q1 due to downstream pipeline friction. Since the internal pressure $p_1$ of the first channel Q1 is relatively low, the molar concentration $c_1$ of the gas dissolved in the medicinal liquid in the first channel Q1 is relatively low, so air is easy to be produced from the medicinal liquid in the first channel Q1 and the produced air can be discharged outside through the passage R. Further, since the internal pressure of the second channel Q2 is relatively high, air is difficult to be produced from the medicinal liquid in the second channel Q2, so it is possible to reduce the possibility of air being produced from the medicinal liquid at the downstream side of the air-passing filter 960.

The capillary channel 820p may be positioned at the downstream side of the second channel Q2. Accordingly, it is possible to keep the second channel Q2 between the boundary filter 980 and the capillary channel 820p at higher pressure. Further, the possibility of air bubbles being produced in the second channel Q2 is remarkably reduced, so it is possible to considerably decrease the possibility of air clogging the capillary channel 820p.

The medicine transfer device 800 may include at least one sealing member 830 fitted between the outer surface of the medicine transfer pipe 820 and the inner surface of the housing 810. The sealing member 830 can prevent a medicinal liquid from flowing between the outer surface of the medicine transfer pipe 820 and the inner surface of the housing 810. The sealing member 830 can surround the medicine transfer pipe 820. The sealing member 830 may be formed in a ring shape. The sealing member 830 may be made of an elastic material such as rubber. The at least one sealing member 830 may include a first sealing member 831 and a second sealing member 832 that are spaced apart from each other.

The medicine transfer device 800 includes the spacer 840 being in contact with the upstream end of the medicine transfer pipe 820. A hole is formed through the center of the spacer 840. A medicinal liquid that has passed through the hole of the spacer 840 flows into the capillary channel 820p.

The spacer 840 may be disposed between the upstream end of the medicine transfer pipe 820 and the intake filter 850, thereby maintaining a gap. The spacer 840 spaces the intake filter 850 from the inlet of the capillary channel 820p such that the intake filter 850 does not block the inlet of the capillary channel 820p.

The medicine transfer device 800 may include an intake filter 850 disposed at the upstream side of the capillary channel 820p. The intake filter 850 may be disposed at the downstream side of the air-passing filter 960. The intake filter 850 may be disposed at the downstream side of the boundary filter 980. The intake filter 850 is disposed such that a medicinal liquid flowing in the channel P passes through the intake filter 850. The intake filter 850 can prevent relatively large air bubbles that have passed through the channel P from clogging the inlet of the capillary channel 820p.

Figure 6:
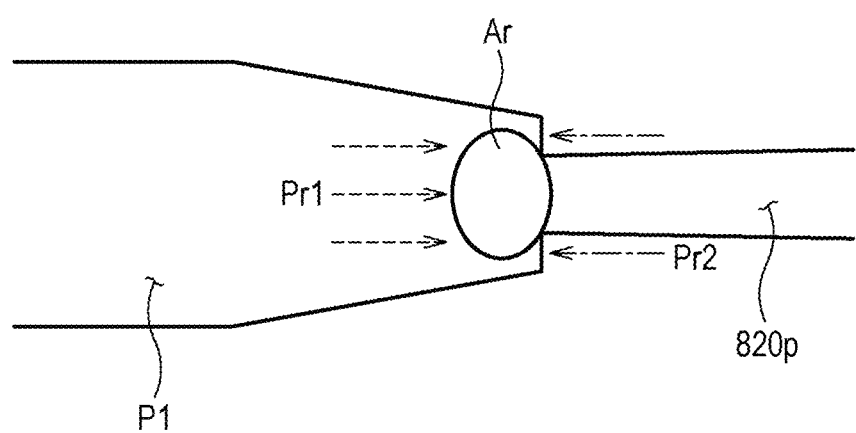
FIG. 6 is a conceptual cross-sectional view for explaining a phenomenon in which the inlet of the capillary channel 820p is clogged with air bubbles Ar.

FIG. 6 is a conceptual cross-sectional view for explaining a phenomenon in which the inlet of the capillary channel 820p is clogged with air bubbles Ar. The problem that the inlet of the capillary channel 820p according to an embodiment is clogged with air bubbles Ar, whereby the flow speed of a medicinal liquid decreases or a medicinal liquid cannot flow into the capillary channel 820p, is described hereafter. This problem is easily generated in an embodiment without the intake filter 850 at the inlet of a medicine transfer pipe.

When relatively large air bubbles Ar are produced by van der Waals forces, pressure Pr1 in the upstream channel P1 that pushes the air bubbles Ar to the downstream side and reacting force Pr2 of the medicine transfer pipe that pushes the air bubbles Ar to the upstream side are in equilibrium, so the air bubbles Ar may clog the inlet of the capillary channel 820p.

In order to solve this problem, the intake filter 850 may be provided in the embodiment referring to FIG. 5. For example, the intake filter 850 may be configured in any one manner of a net structure and a dense fiber structure. The net structure or the dense fiber structure can induce a liquid to be absorbed in the intake filter 850 and flow into the inlet of a medicine transfer pipe by avoiding bubbles clogging the inlet. The net structure may also break large bubbles into small bubbles. The intake filter 850 having a net structure may be made of a hydrophobic material or a hydrophilic material. The intake filter 850 having a dense fiber structure may be preferably made of a hydrophilic material.

For example, the intake filter 850 may be a filter made of a hydrophilic material. The intake filter 850 made of a hydrophilic material can prevent air bubbles Ar from clogging the inlet of the capillary channel 820p by breaking the air bubbles Ar at the upstream side of the capillary channel 820p. When the intake filter 850 made of a hydrophilic material is provided, a medicinal liquid can permeate into and pass through the intake filter 850 even in the state that air bubbles Ar are caught in the upstream side of the intake filter 850.

As another example, the intake filter 860 may be a filter made of a hydrophobic material having a net with relatively large meshes such that a medicinal liquid can pass through the intake filter 860. In this case, the intake filter 850 made of a hydrophobic material can prevent air bubbles Ar from clogging the inlet of the capillary channel 820p by breaking the air bubbles Ar at the upstream side of the capillary channel 820p.

Figure 7:
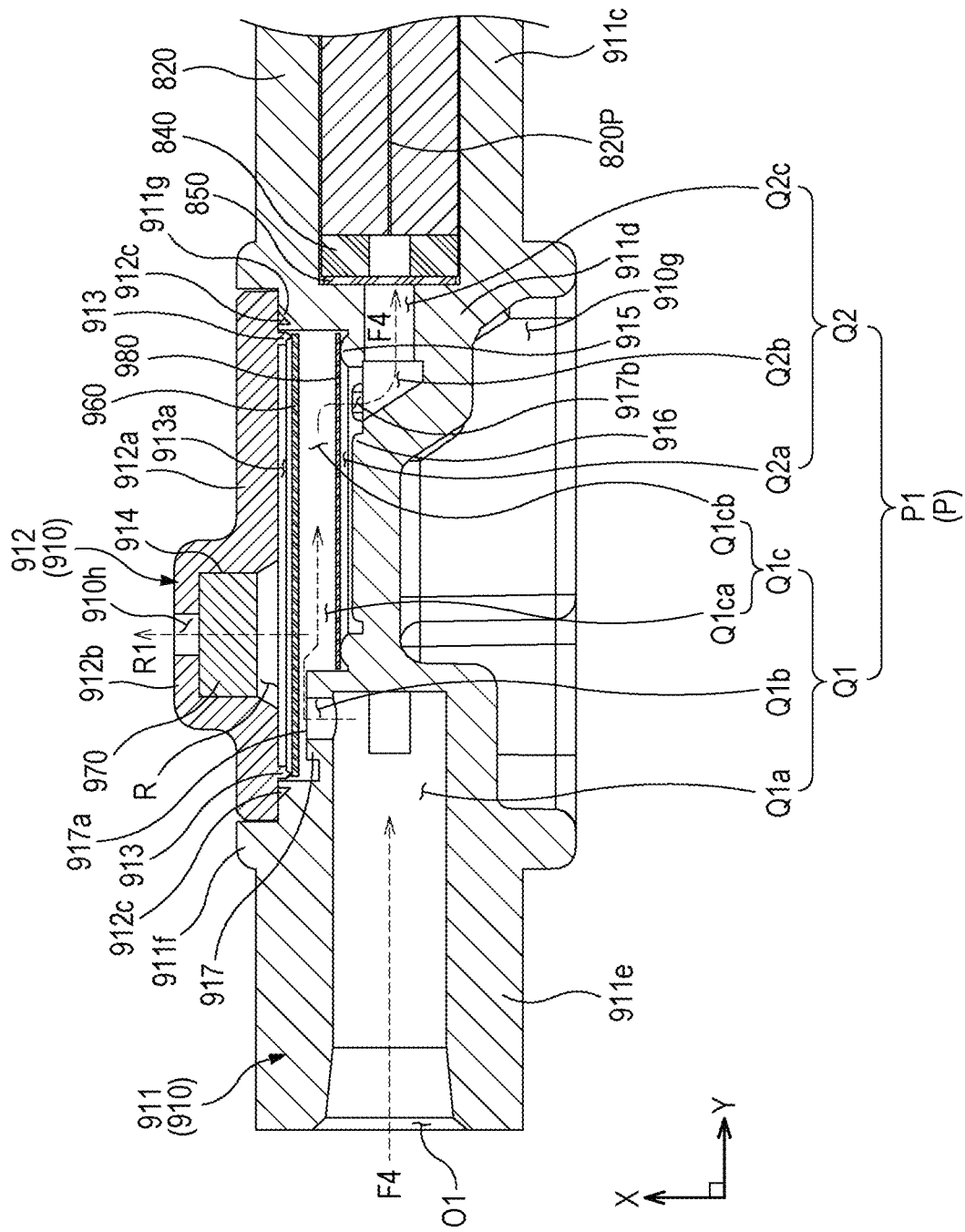
FIG. 7 is a partial enlarged vertical cross-sectional view of FIG. 2.
Figure 8:
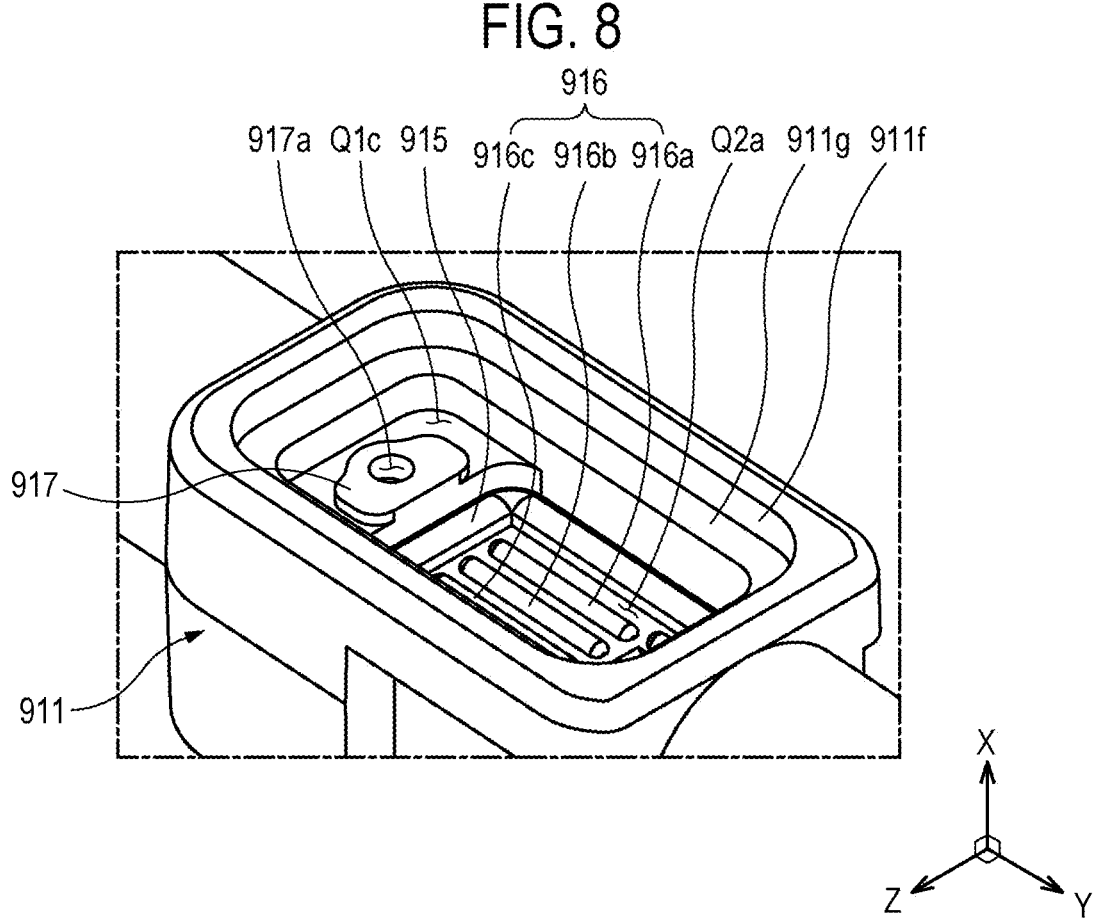
FIG. 8 is a perspective view showing the portion E1 of FIG. 4 in a predetermined direction.
Figure 9:
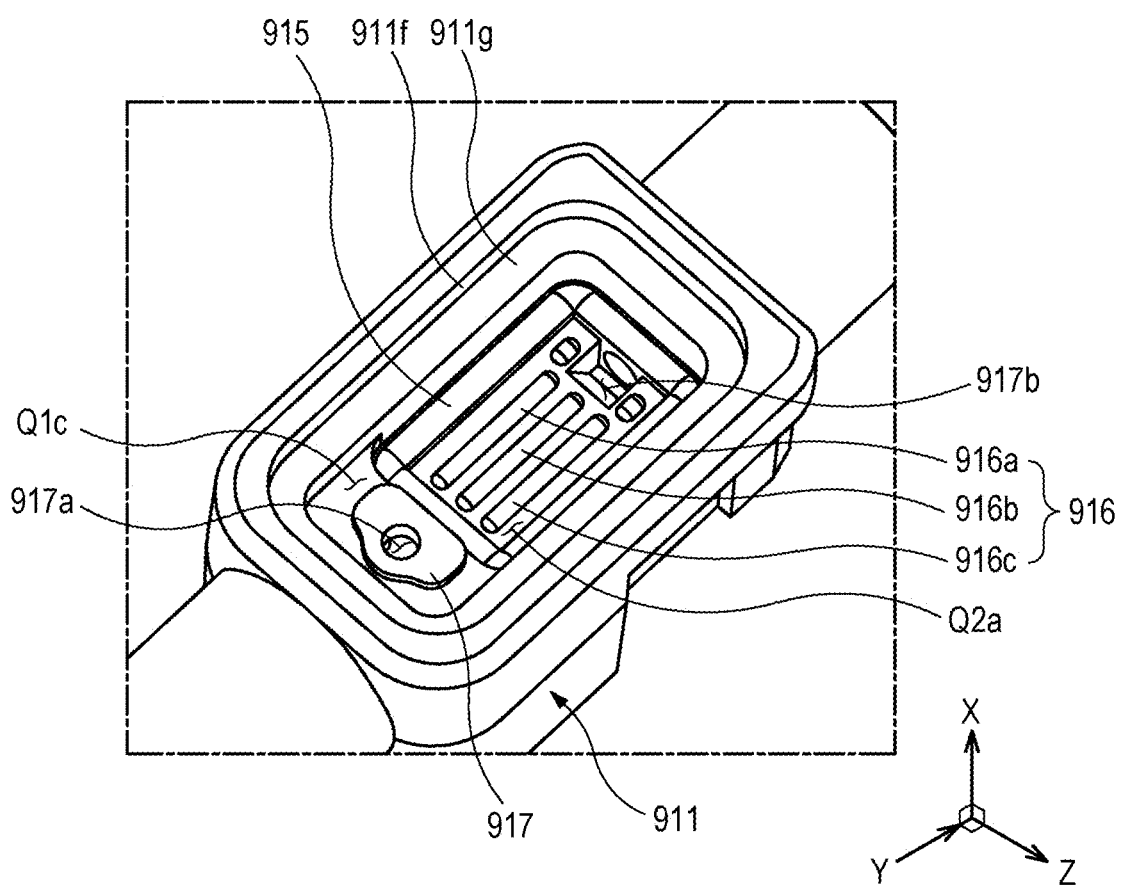
FIG. 9 is a perspective view showing the portion shown in FIG. 8 viewed in another direction.

FIG. 7 is a partial enlarged vertical cross-sectional view of FIG. 2. FIG. 8 is a perspective view showing the portion E1 of FIG. 4 in a predetermined direction. FIG. 9 is a perspective view showing the portion shown in FIG. 8 viewed in another direction.

Referring to FIGS. 7 to 9, the medicinal liquid channel P includes the filtering channels Q1 and Q2 formed in the filter housing 910. The filtering channels Q1 and Q2 include the first channel Q1 and the second channel Q2. The channel P includes a contact channel Q1c configured such that a medicinal liquid therein comes in contact with the air-passing filter 960.

The contact channel Q1c may be positioned at the upstream side or at the downstream side of the capillary channel 820p. The contact channel Q1c is disposed close to the capillary channel 820p. The channel length between the contact channel Q1c and the capillary channel 820p is smaller than the entire channel length of the capillary channel 820p.

In the embodiment of FIGS. 7 to 9, the contact channel Q1c is positioned at an upstream side of the capillary channel 820p such that the medicinal liquid that has passed through the contact channel Q1c flows into the capillary channel 820p. Accordingly, it is possible to remove air mixed with a medicinal liquid to be sent to the capillary channel 820p and to reduce the possibility of the capillary channel 820p abnormally operating due to air.

The first channel Q1 includes the contact channel Q1c. The first channel Q1 includes a facing channel Q1b connected to the upstream side of the contact channel Q1c. The facing channel Q1b is configured to discharge a medicinal liquid into the contact channel Q1c toward the air-passing filter 960 in the first direction X. The facing channel Q1b may extend in the first direction X. The first channel Q1 may include an intake channel Q1a connected to the intake port O1 of the first channel Q1 and positioned at the upstream side of the contact channel Q1c. The intake channel Q1a may be connected to the upstream side of the facing channel Q1b.

The second channel Q2 includes a discharge channel Q2c that guides a medicinal liquid to be discharged through the outlets of the filtering channels Q1 and Q2 of the second channel Q2. The second channel Q2 includes an extension channel Q2b including a portion extending in a direction opposite to the first direction X. The extension channel Q2b curves or bends while extending. The extension channel Q2b may be connected to the upstream side of the discharge channel Q2c. The second channel Q2 may have a gap Q2a between the boundary filter 980 and the housing 810. The extension channel Q2b may be connected to the downstream side of the gap Q2a.

The filtering channels Q1 and Q2 may be configured to curve or bend at least once or more. The filtering channels Q1 and Q2 may be configured to curve or bend in the first direction X at least once or more. The filtering channels Q1 and Q2 may have a portion where a portion extending in the second direction Y and a portion extending in the first direction are connected to each other. Accordingly, it is possible to increase the possibility of air hitting against the interface of the filtering channels Q1 and Q2 that guides the flow of a medicinal liquid, and it is possible to more smoothly discharge air through the air-passing filter 960.

In an embodiment, the intake channel Q1a extends in the second direction Y. The facing channel Q1b extends in the first direction X at the downstream side portion of the intake channel Q1a. The facing channel Q1b has an outlet 917a being open in the first direction X. The facing channel Q1b connects the intake channel Q1a and the contact channel Q1c to each other. In an embodiment, the contact channel Q1c extends in the second direction Y. The contact channel Q1c includes a space between the air-passing filter 960 and the boundary filter 980. The gap Q2a of the second channel Q2 extends in the second direction Y. The gap Q2a is positioned in a direction opposite to the first direction X of the contact channel Q1c. The gap Q2a is positioned in a direction opposite to the first direction X of the contact channel Q1c with the boundary filter 980 therebetween. The extension channel Q2b includes a portion curving or bending in the second direction from the direction opposite to the first direction X. The extension channel Q2b has an inlet 917b being open in the first direction X. The discharge channel Q2c extends in the second direction.

The surface facing the first channel Q1 of the air-passing filter 960 may extend along a side of the first channel Q1. Although the air-passing filter 960 extends flat along a side of the first channel Q1, an air-passing filter 960 according to another embodiment not shown may extend while curving or bending along a side of the first channel Q1. Accordingly, the contact area and contact time between the air-passing filter 960 and the medicinal liquid in the channel P can be increased, and various relevant examples about this configuration of the air-passing filter 960 and the channel P are described.

The air-passing filter 960 may be configured to pass air in the first direction X. The air-passing filter 960 may extend in the second direction Y. The length in the second direction Y may be larger than the thickness in the first direction X of the air-passing filter 960. The contact channel Q1c may be formed such that the length in the second direction Y is larger than the length in the first direction X facing the air-passing filter 960. The air-passing filter 960 may extend along the length of the contact channel Q1c in the second direction Y.

The air-passing filter 960 may be formed in a plate shape with two sides. The air-passing filter 960 may extend in the second direction Y and a third direction Z. The term "third direction Z" used herein may be defined a direction perpendicular to the first direction X and the second direction Y. The length in the second direction Y and the length in the third direction Z may be larger than the thickness in the first direction X of the air-passing filter 960. The contact channel Q1c may be formed such that the length in the third direction Z is larger than the length in the first direction X. The air-passing filter 960 may extend along the length of the contact channel Q1c in the third direction Z.

A downstream side portion Q1cb of the contact channel Q1c may be spaced apart from an upstream side portion Q1ca of the contact channel Q1c in the second direction Y. The length in the second direction Y may be larger than the length in the third direction Z of the air-passing filter 960. The contact channel Q1c may be formed such that the length in the second direction Y is larger than the length in the third direction Z.

The upstream side portion Q1ca means a portion relatively close to the opening 917a formed such that a medicinal liquid flows into the contact channel Q1c and the downstream side portion Q1cb means a portion relatively close to the opening 917b formed such that a medicinal liquid is discharged from the contact channel Q1c. In the embodiment, a medicinal liquid in the contact channel Q1c passes through the boundary filter 980 in order to be discharged through the opening 917b.

The air-passing filter 960 may cover the side of the first direction X of the contact channel Q1c. The air-passing filter 960 may cover about 90% of the side of the first direction X of the contact channel Q1c.

A cross-section perpendicular to the up-downstream direction of the contact channel Q1c may be elongated to a side. The cross-section perpendicular to the up-downstream direction of the contact channel Q1c may be formed such that the length in the third direction Z perpendicular to the first direction X is larger than the length in the first direction X.

The area of the air-passing filter 960 may be larger than the area of the boundary filter 980. The length in the first direction X of the air-passing filter 96 may be larger than the length in the first direction X of the boundary filter 980.

The boundary filter 980 may be configured to pass a medicinal liquid in the opposite direction to the first direction X. The boundary filter 980 may extend in the second direction Y. The length in the second direction Y may be larger than the thickness in the first direction X of the boundary filter 980. The boundary filter 980 may extend along the length of the contact channel Q1c in the second direction Y.

The boundary filter 980 may be formed in a plate shape with two sides. The boundary filter 980 may extend in the second direction Y and a third direction Z. The length in the second direction Y and the length in the third direction Z may be larger than the thickness in the first direction X of the boundary filter 980. The boundary filter 980 may extend along the length of the contact channel Q1c in the third direction Z. The length in the second direction Y may be larger than the length in the third direction Z of the boundary filter 980. The boundary filter 980 may cover a portion of the opposite side of the first direction X of the contact channel Q1c.

The filter housing 910 may have a facing protrusion 917 that protrudes in the first direction X to face the air-passing filter 960. The facing protrusion 917 may be positioned in the contact channel Q1c. The outlet 917a of the facing channel Q1b may be formed at a protrusive end of the facing protrusion 917.

A first spacing distance in the first direction X between the protrusive end of the facing protrusion 917 and the air-passing filter 960 may be shorter than a second spacing distance in the first direction X between any other component in the contact channel Q1c and the air-passing filter 960. For example, the first spacing distance is shorter than the spacing distance in the first direction X between the air-passing filter 960 and the boundary filter 980.

The filter housing 910 includes a boundary filter seat 915 to which the boundary filter 980 is coupled. The boundary filter seat 915 may extend along an edge of boundary filter 980. The boundary filter seat 915 may be formed on the filter body 911. The boundary filter seat 915 may protrude in the first direction X from the inner surface of the housing 810. The boundary filter 980 can be coupled to the boundary filter seat 915 in various ways such as UV (Ultraviolet) bonding, ultrasonic bonding, and forcible fitting.

The filer housing part 910 may include a space-maintaining portion 916 protruding toward the boundary filter 980 in order to maintain the gap Q2a between a surface opposite to the surface facing the first channel Q1 of the boundary filter 980 and the inner surface of the housing 810. The gap Q2a constitutes a portion of the second channel Q2. The space-maintaining portion 916 can prevent deterioration of moisture permeation efficiency due to the boundary filter 980 sticking to the inner surface of the housing 810 when the boundary filter 980 is wetted with a liquid.

The space-maintaining portion 916 may be formed on the filter body 911. A protrusive end in the first direction X of the space-maintaining portion 916 may be positioned in the direction opposite to the first direction X further than the protrusive end in the first direction X of the boundary filter seat 915. The space-maintaining portion 916 may protrude in the first direction X and extend in the second direction. The space-maintaining portion 916 may have at least one rib. A plurality of space-maintaining portions 916a, 916b, and 916c may be arranged and spaced apart from each other in the third direction Z. A plurality of space-maintaining portions 916a, 916b, and 916c may extend in parallel in the second direction Y.

The filter body 911 includes a cap guide 911f that guides the coupling position of the vent cap 912. The cap guide 911f may protrude in the first direction X from the filter body 911. The cap guide 911f may surround the circumference of the cover portion 912a of the vent cap 912.

The filter body 911 may have a counter-cap coupling portion 911g coupled to cap coupling portion 912c of the vent cap 912. The counter-cap coupling portion 911g may have a surface facing the first direction X.

The vent cap 912 may include the cap coupling portion 912c extending along the edge of the cover portion 912a. The cap coupling portion 912c is formed on the side opposite to the first direction X of the vent cap 912. In the embodiment, the cap coupling portion 912c is coupled to the counter-cap coupling portion 911g in a fusion bonding manner according to ultrasonic bonding, but the vent cap 912 can be coupled to the filter body 911 in various ways such as UV (Ultraviolet) bonding and/or forcible fitting.

The filter housing 910 includes an air-passing filter seat 913 to which the air-passing filter 960 is coupled. The air-passing filter seat 913 may protrude in the opposite direction to the first direction X. The air-passing filter seat 913 may extend along the edge of the air-passing filter 960. The air-passing filter seat 913 may be formed on the inner surface of the vent cap 912. The air-passing filter seat 913 may be positioned in the opposite side to the first direction X of the cover portion 912a of the vent cap 912. In the embodiment, the air-passing filter 960 is coupled to the air-passing filter seat 913 by fusion bonding according to ultrasonic bonding, but the air-passing filter 960 may be coupled to the air-passing filter seat 913 in various ways such as UV (Ultraviolet) bonding and/or forcible fitting.

A gap 913a may be formed between the side opposite to the side facing the first channel Q1 of the air-passing filter 960 and the inner surface of the housing 810. The air-passing filter seat 913 protrudes, thereby spacing the air-passing filter 960 from the inner surface of the vent cap 912. The gap 913a constitutes a portion of the air passage R.

An air-passing filter seat 810 may protrude such that the rear surface of the air-passing filter 960 is spaced apart from the inner surface of the housing 910. The air-passing filter seat 913 may protrude toward the contact channel Q1c from the inner surface of the housing 810 and may extend along the circumference of the air-passing filter 960.

The filter housing 910 may include a secondary air-passing filter seat 914 forming a groove 914a in which the secondary air-passing filter 970 is inserted. The secondary air-passing filter seat 914 may be formed in the vent cap 912. The secondary air-passing filter seat 914 may be formed on the inner surface of the vent protrusion 912b. In the embodiment, the secondary air-passing filter 970 is coupled to the secondary air-passing filter seat 914 by forcible fitting, but is not necessarily limited thereto. The secondary air-passing filter seat 914 may be referred to as an additional air-passing filter seat 914.

Figure 10:
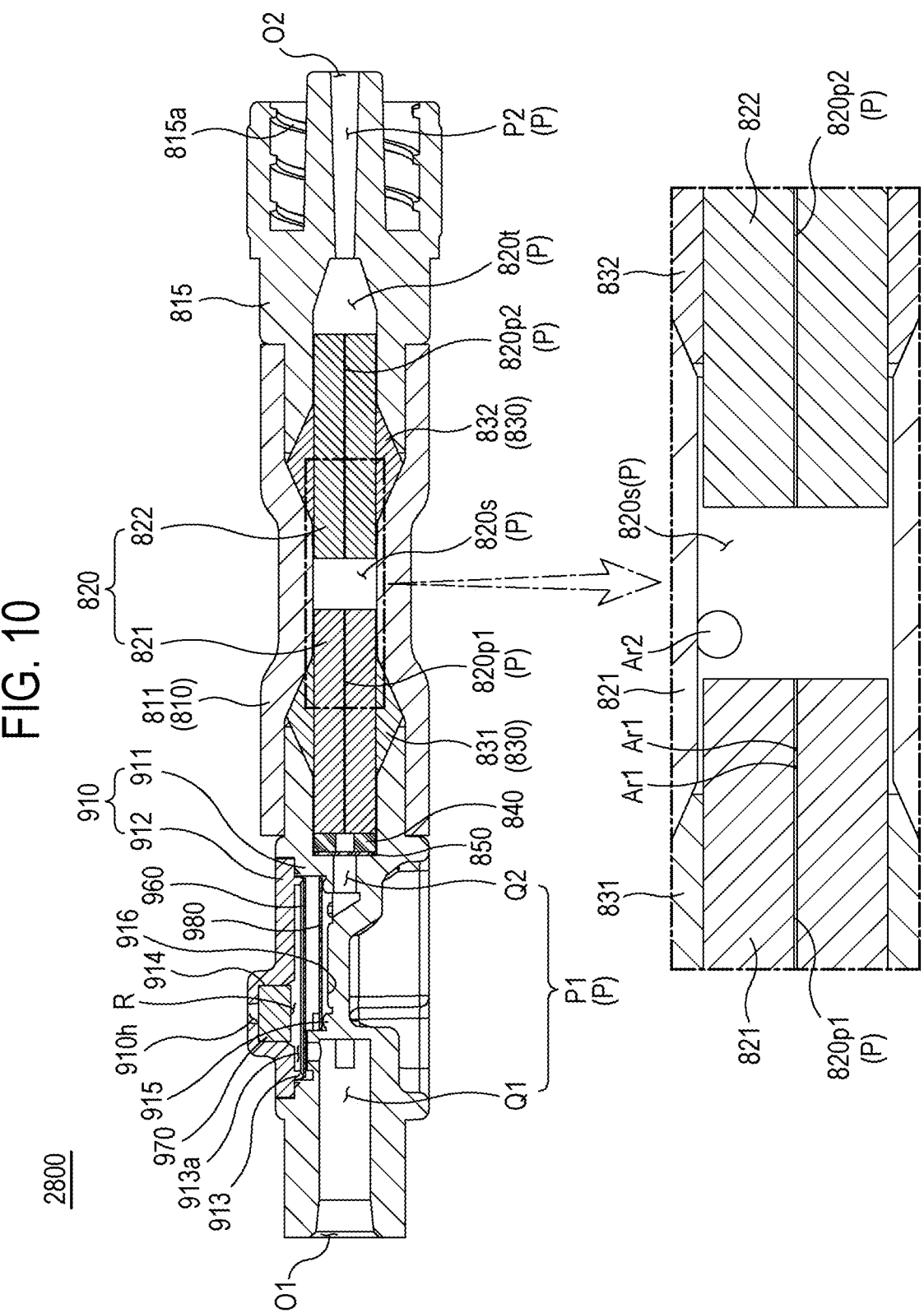
FIG. 10 is a vertical cross-sectional view of a filter-integrated medicine transfer device 2800 according to a second embodiment.

FIG. 10 is a vertical cross-sectional view of a filter-integrated medicine transfer device 2800 according to a second embodiment. Referring to FIG. 10, at least one medicine transfer pipe 820 includes a plurality of medicine transfer pipes 820 each having a capillary channel 820p constituting a portion of the channel P. In this embodiment, the medicine transfer device 2800 includes only two medicine transfer pipes 821 and 822, but is not limited thereto and may include three or more medicine transfer pipes. The medicine transfer device 2800 includes a housing 810 to which the medicine transfer pipes 820 are coupled.

The medicine transfer pipes 820 include a first medicine transfer pipe 821 having a first capillary channel 820p1 constituting a portion of the channel P and a second medicine transfer pipe 822 having a second capillary channel 820p2 constituting a portion of the channel P. The second capillary channel 820p2 is disposed further downstream than the first capillary channel 820p1 such that a medicinal liquid that has passed through the first capillary channel 820p1 flows therein.

An intervention space 820s is formed between two medicine transfer pipes 821 and 822 adjacent to each other in the up-downstream direction in the medicine transfer device 2800. A channel cross-sectional area of the intervention space 820s is larger than a channel cross-sectional area of the first capillary channel 820p1 and a channel cross-sectional area of the second capillary channel 820p2. The term "channel cross-sectional area" used in the present disclosure means a cross-sectional area of a channel cut perpendicularly to the up-downstream direction.

The intervention space 820s is formed between the first medicine transfer pipe 821 and the second medicine transfer pipe 822 in the housing 810. The intervention space 820s is configured such that a medicinal liquid that has passed through the first capillary channel 820p1 flows therein. The intervention space 820s is configured such that the medicinal liquid therein moves to the second capillary channel 820p2.

The inner surface of the housing 810 may form at least a portion of the boundary of the intervention space 820s. The first medicine transfer pipe 821 may form a portion of the boundary of the intervention space 820s. The second medicine transfer pipe 822 may form a portion of the boundary of the intervention space 820s.

The first medicine transfer pipe 821 and the second medicine transfer pipe 822 are coupled to the housing 810. The first capillary channel 820p1, the intervention space 820s, and the second capillary channel 820p2 may be sequentially positioned on the channel P. The filtering channels Q1 and Q2 may be disposed at the upstream side of the first capillary channel 820p1. The contact channel Q1c may be disposed at the upstream side of the first capillary channel 820p1.

The at least one sealing member 830 includes a first sealing member 831 fitted between the outer surface of the first medicine transfer pipe 821 and the inner surface of the housing 810. The at least one sealing member 830 includes a second sealing member 832 fitted between the outer surface of the second medicine transfer pipe 822 and the inner surface of the housing 810. The spacer 840 may be in contact with the upstream end of the first medicine transfer pipe 821.

Figure 11:
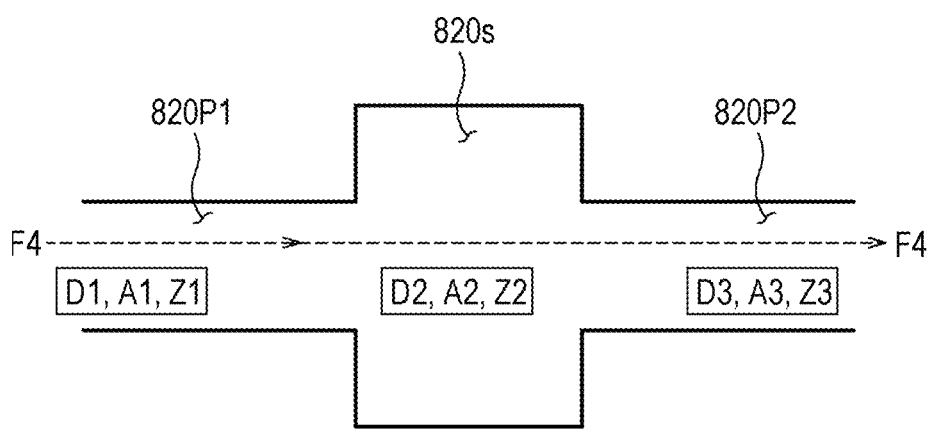
FIG. 11 is a conceptual cross-sectional view for explaining a function of an intervention space 820s between two capillary channels 820p1 and 820p2.

FIG. 11 is a conceptual cross-sectional view for explaining a function of an intervention space 820s between two capillary channels 820p1 and 820p2. The operational principles of embodiments of the present disclosure are described hereafter with reference to FIGS. 10 and 11.

When a medicinal liquid flows, the flow speed increases in the extension tube 300 relatively less in the channel cross-sectional area (diameter) than in the chamber 110 (see FIG. 1), so the pressure decreases in accordance with Bernoulli's principle. As the pressure decreases in the extension tube 300, the air dissolved in the medicinal liquid in the extension tube 300 can be discharged in accordance with Henry's law. The air exists in an air bubble state in the extension tube 300. Further, even though there is an external filter device 500, air that has not been completely filtered out by the external filter device 500 or the air produced at the downstream side of the external filter device 500 may reach the inside of the medicine transfer device 800.

Further, when the medicinal liquid flowing through the channel of the extension tube 300 and the upstream channel P1 of the medicine transfer device 800, which have relatively large channel cross-sectional areas, flows into the capillary channel 820p, the flow speed relatively increases, so the pressure decreases in accordance with Bernoulli's principle. Since the pressure decreases in the capillary channel 820p, an environment in which substances dissolved in the medicinal liquid (e.g., dissolved oxygen or dissolve carbon dioxide) in the capillary channel 820p are easily discharged into the air is created in accordance with Henry's law.

In this situation, the medicinal liquid keeps decreasing in pressure while flowing through the capillary channel 820p, so a dissolved substance in a medicinal liquid is easily discharged into the air as it goes the downstream side in any one capillary channel. For example, as it goes to the downstream side of the medicinal liquid transfer pipe, the internal pressure decreases and much air is discharged from the medicinal liquid, so the flow of the liquid may become difficult. This is because the channel cross-sectional area of the capillary channel 820p is very small, and accordingly, the loss of head per channel length is relatively large. Such a pressure drop in a capillary channel can be theoretically confirmed through Bernoulli's principle.

An assumed situation according to the following formula is set as an embodiment with reference to FIG. 5.

$$\gamma1=\gamma2,\ Z1=Z2=Z3,\ D1=D3,\ A1=A3,\ A2=400A1$$

$\gamma1$ is specific gravity of a medicinal liquid in the first capillary channel 820p1 and $\gamma2$ is specific gravity of a medicinal liquid in the intervention space 820s, in which the specific gravity can be briefly expressed as $\gamma$ under the assumption that the specific gravity is the same at any position. $\rho$ is the density of a medicinal liquid. Z1 is the height of the first capillary channel 820p1, Z2 is the height of the intervention space 820s, and Z3 is the height of the second capillary channel 820p2, in which the heights may be changed, but it is assumed that the height are the same values.

D1 is the diameter of the first capillary channel 820p1, D2 is the diameter of the intervention space 820s, and D3 is the diameter of the second capillary channel 820p2. Further, A1 is the channel cross-sectional area of the first capillary channel 820p1, A2 is the channel cross-sectional area of the intervention space 820s, and A3 is the channel cross-sectional area of the second capillary channel 820p2. For example, when D2 is 1 mm and D1 is 0.05 mm, D2=20×D1 and A2=400×A1 are satisfied.

Q is a volume flow rate per unit time and V is a flow speed, and in this case, Q=AV is satisfied. The volume flow rate per unit time is the same in all of the first capillary channel 820p1, the intervention space 820s, and the second capillary channel 820p2, so the following formulae are satisfied on the basis of the above A2=400×A1.

$$V1=400\times V2$$

$$V2=V1/400$$

V1 is a flow speed in the first capillary channel 820p1, and V2 is a flow speed in intervention space 820s.

Further, using Bernoulli's principle, the following formula can be induced on the basis of the states of the first capillary channel 820p1 and the intervention space 820s.

$$P1/\gamma 1 + V1^2/2g + Z1 = P2/\gamma 2 + V2^2/g + Z2 + h1$$

Herein, g is the acceleration of gravity. Further, h1 is a loss of head and h1=hf+hb may be satisfied. hf is a loss of head due to friction in a pipe and hb is a loss of head due to other factors except for the friction in a pipe. Further, P1 is fluid pressure in the first capillary channel 820p1 and P2 is fluid pressure in the intervention space 820s. The following formula is obtained by substituting Z1=Z2 into the above formula.

$$P1/\gamma 1 + V1^2/2g = P2/\gamma 2 + V2^2/2g + h1$$

The following formula is obtained by substituting V1=400×V2 into the above formula.

$$P1/\gamma + (400*V2)^2/2g = P2/\gamma + V2^2/2g + h1$$

The following Formula 1 is derived by arranging the above formula.

$$(P1-P2)/\gamma = (V2^2(1\text{-}160000))/2g + h1 \qquad [\text{Formula 1}]$$

Assuming that the pressure at an upstream position is defined as P11 and the pressure at a downstream position is defined as P12 in the same first capillary channel 820p1, and the loss of head from the upstream position to the downstream position is defined as h1p, the following formula is obtained.

$$P11/\gamma + V1^2/2g = P12/\gamma + V1^2/2g + h1p$$

The following Formula 2 is derived by arranging the above formula.

$$(P11-P12)/\gamma = h1p \qquad [\text{Formula 1}]$$

It can be seen from Formula 2 that a loss of head h1p is generated when a liquid flows into one capillary channel and pressure drops is generated as much as the generated loss of head h1p (P11>P12). Accordingly, it is found that dissolved substances in a medicinal liquid are more easily discharged into the air moving downstream in the same pipe.

In an embodiment that uses only one medicine transfer pipe having a predetermined length to set the flow rate of a medicinal liquid at a predetermined level, the length of the only one capillary channel is long, so the loss of head is relatively larger at the downstream side portion than at the upstream end of the capillary channel and a relatively large amount of air is produced at the downstream side portion of the capillary channel, whereby the possibility of clogging of the capillary channel increases.

However, referring to FIGS. 10 and 11, in the embodiment that divides the medicine transfer pipe 820 having a predetermined length into several pieces to set the flow rate of a medicinal liquid at a predetermined level, the loss of head of the liquid flowing through one capillary channel 820p1 or 820p2 is decreased, whereby a relatively small amount of air is produced in the capillary channel 820p1 and 820p2. Accordingly, the possibility that the capillary channel is clogged with air bubbles Ar1 is remarkably reduced. Even if air bubbles Ar1 are produced in the capillary channels 820p1 and 820p2, the channel lengths that the air bubbles Ar1 moves to reach the outlets of the capillary channels 820p1 and 820p2 are small, so the possibility that the capillary channel 820p is clogged with air bubbles Ar1 is remarkably reduced.

Further, referring to FIGS. 10 and 11, even if small air bubbles Ar1 are produced in the first capillary channel 820p1, air bubbles Ar2 are gathered and contained in the intervention space 820s, so only a medicinal liquid with air bubbles removed can flow into the second capillary channel 820p2 at the downstream side. Since the medicinal liquid with air bubbles removed flows into the second capillary channel 820p2, the medicinal liquid can smoothly flow at a predetermined level.

Figure 12:
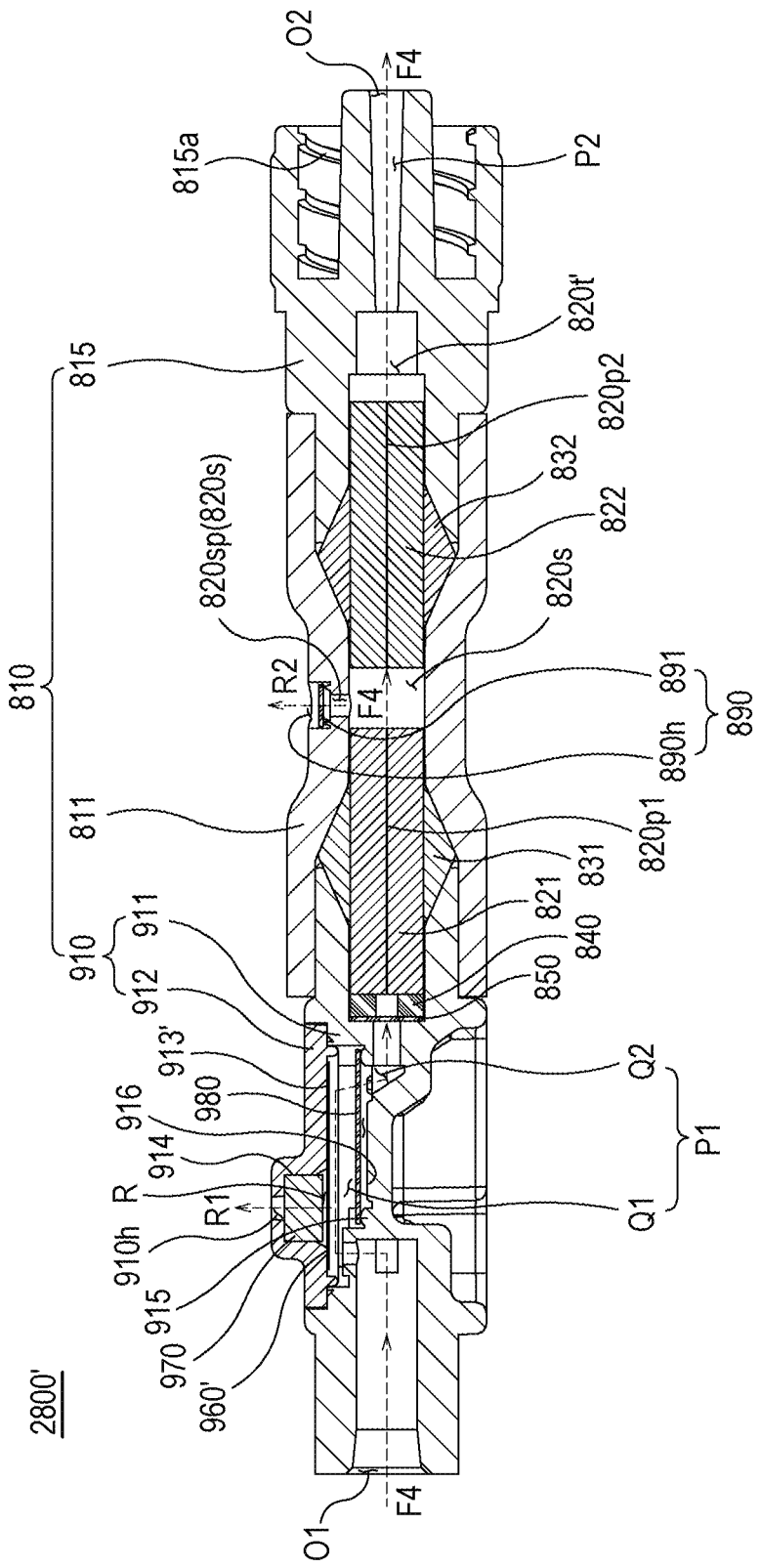
FIG. 12 is a vertical cross-sectional view of a modification of the medicine transfer device 2800 of FIG. 10.

FIG. 12 is a vertical cross-sectional view of a modification of the medicine transfer device 2800 of FIG. 10. Referring to FIG. 12, the medicine transfer device 2800 may further have an air vent 890 configured to connect the intervention space 820s to the external space such that air in the intervention space 820s and air in a medicinal liquid are discharged to the external space. A vent hole 890h of the air vent 980 may be formed in the medicine transfer pipe housing 811.

The air vent 890 includes a hydrophobic air-passing filter 891. The air vent 890 has an air channel (not shown) through which the air in the intervention space 820s passes (see the arrow R2). The air-passing filter 891 forms the boundary between the air passage of the air vent 890 and the intervention space 820s.

The intervention space 820s may further include an air passage connection space 820sp configured to be connected with the air passage of the air vent 890. The air passage connection space 820sp may be formed at a radial end of the intervention space 820s. The air-passing filter 891 forms the boundary between the air passage of the air vent 890 and the air passage connection space 820sp.

The rear surface of the air-passing filter 960' of the medicine transfer device 2800' is in close contact with the inner surface 913' of the housing 810, so an air passage R can be formed without the gap 913a described above.

The boundary of the downstream space 820t' of the medicine transfer device 2800' includes a stepped portion. On the other hand, the boundary of the downstream space 820t of FIG. 10 includes an inclined surface narrowing toward the downstream channel P2. Further, the downstream space may be configured in various shapes.

In another embodiment that is not shown, the medicine transfer device 800 may be configured without the downstream space 820t of FIG. 10. The downstream end of the second medicine transfer pipe 822 may be latched in contact with the inner surface of a housing (e.g., the downstream housing part 815). In another embodiment not shown, a spacer may be disposed between the downstream end of the second medicine transfer pipe 822 and the inner surface of the housing 810. Further, a second capillary channel 820p2 and a downstream channel P2 may be sequentially connected in a channel P.

Figure 13:
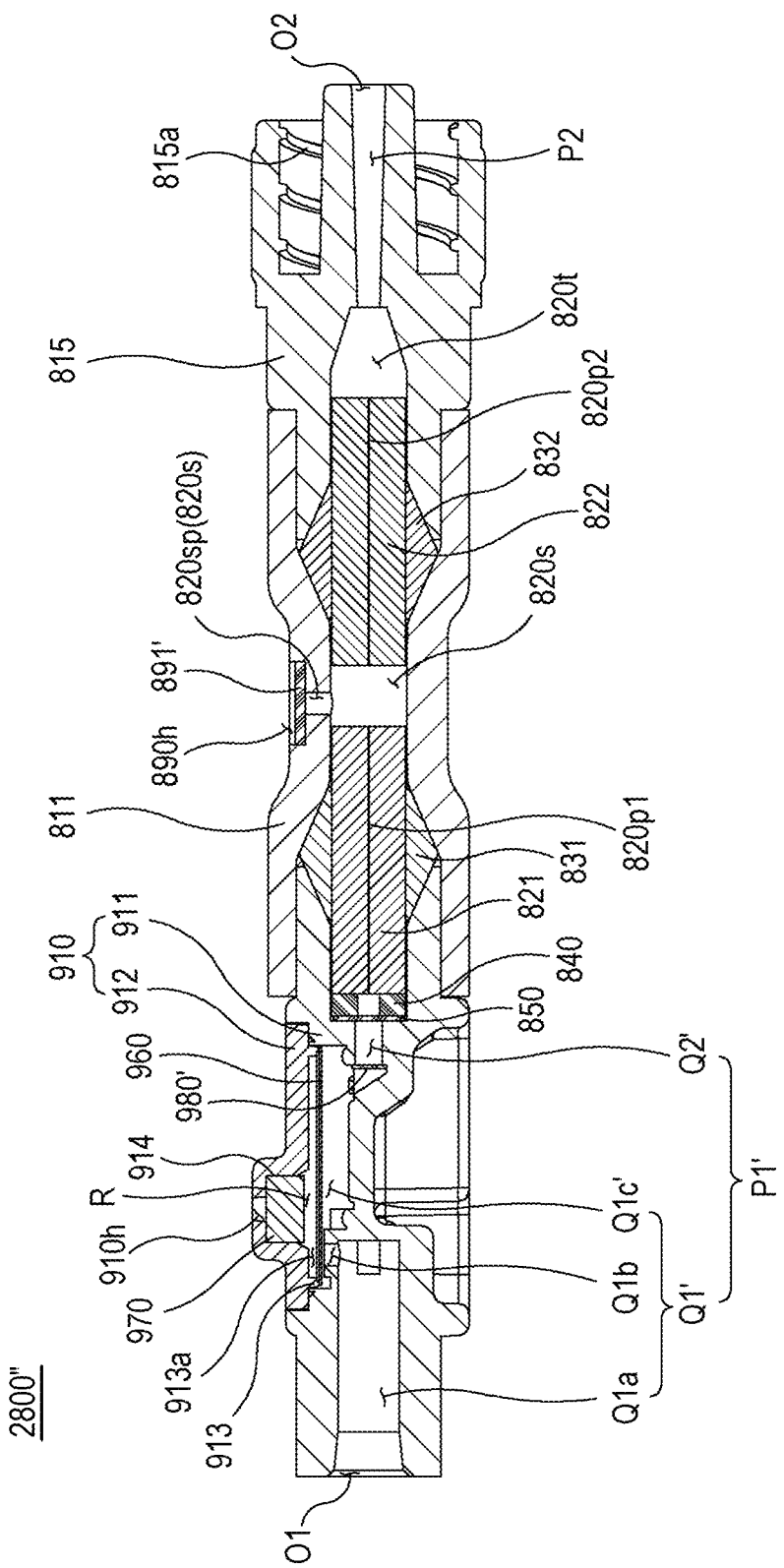
FIG. 13 is a vertical cross-sectional view of another modification of the medicine transfer device 2800 of FIG. 10.

FIG. 13 is a vertical cross-sectional view of another modification of the medicine transfer device 2800 of FIG. 10. Referring to FIG. 13, a boundary filter 980' may be implemented in various shapes and various arrangement manners. The boundary filter 980' may be disposed to have a thickness in a direction Y facing the inlet of the capillary channel 820p. Various shapes and boundaries of a first channel Q1' and a second channel Q2' may be implemented. The second channel Q2' includes the discharge channel Q1c described above and may not include the extension channel Q2b and the gap Q2a. The first channel Q1' may have a contact channel Q1c having various shapes. The position and the arrangement direction of the boundary filters 980 and 980' shown in FIGS. 12 and 13 are only some examples and are not necessarily limited thereto.

The length of an air-passing filter 891' of the air vent 890 in the up-downstream direction in the medicine transfer device 2800" may be longer than the channel length of the intervention space 820s. Further, the air-passing filter 891' may be configured in various shapes and may be coupled to the housing 810 in various ways.

Figure 14:
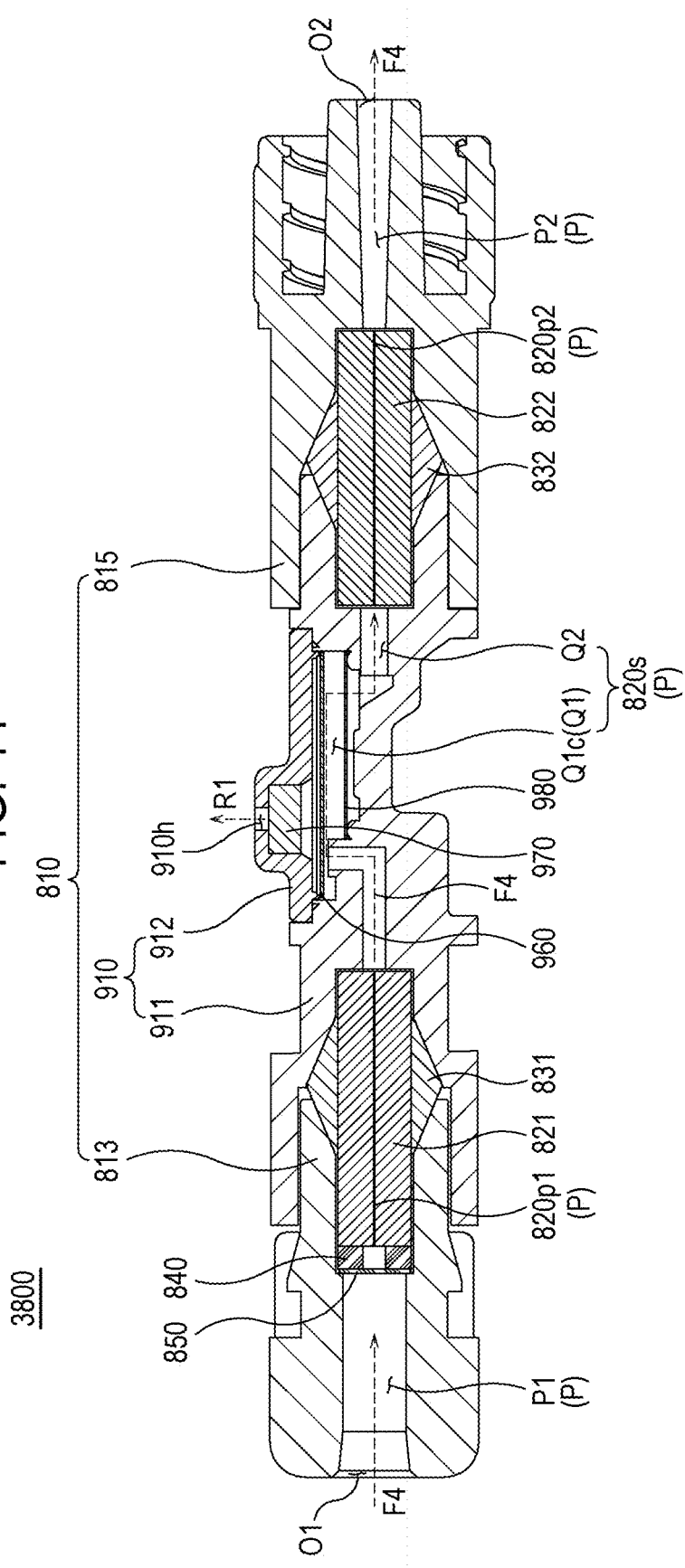
FIG. 14 is a vertical cross-sectional view of a filter-integrated medicine transfer device 3800 according to a third embodiment.
Figure 15:
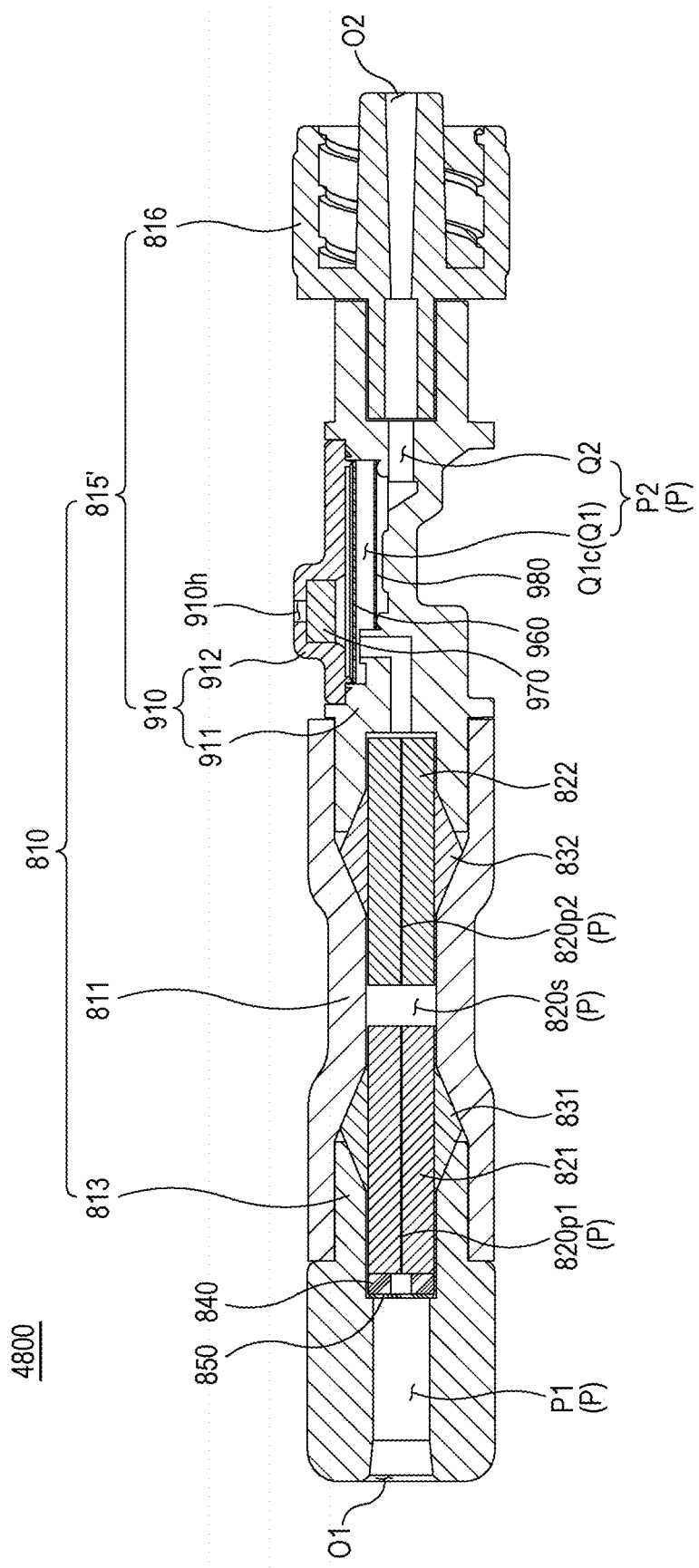
FIG. 15 is a vertical cross-sectional view of a filter-integrated medicine transfer device 4800 according to a fourth embodiment.
Figure 16:
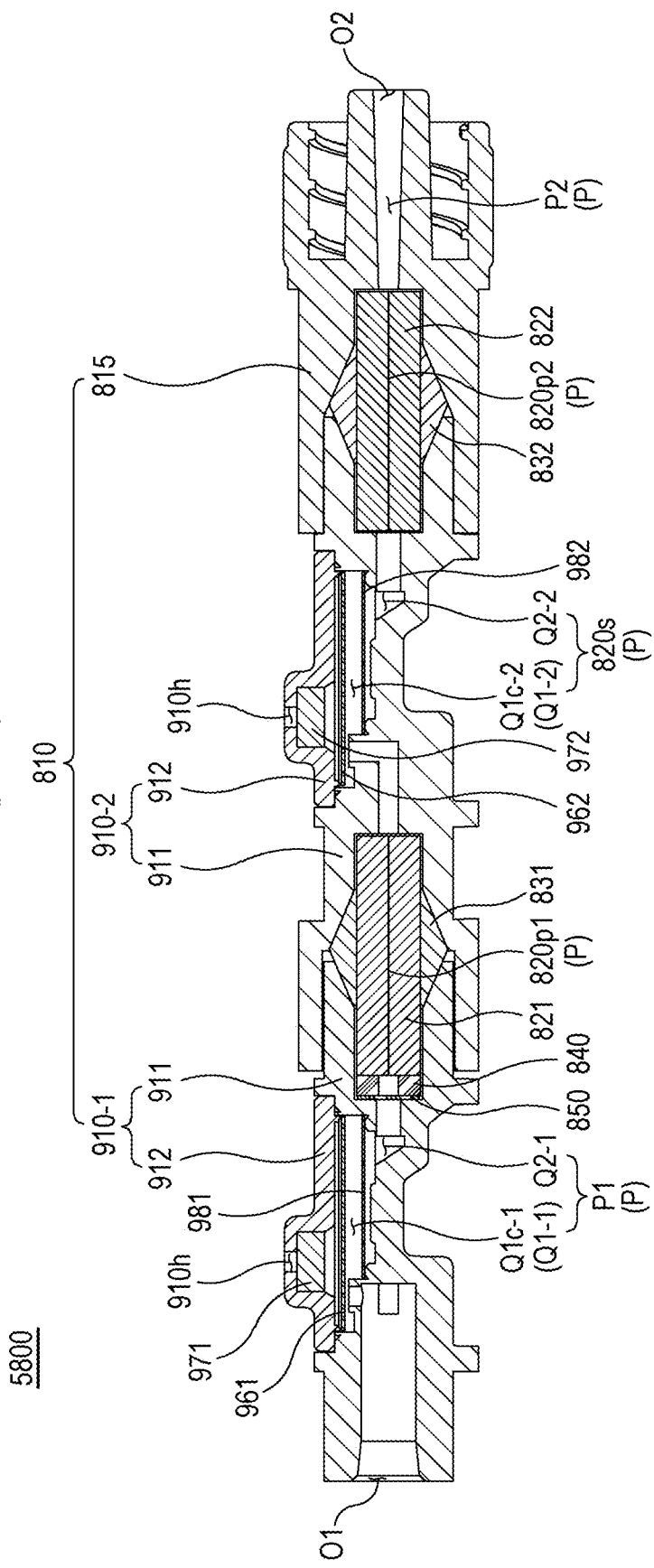
FIG. 16 is a vertical cross-sectional view of a filter-integrated medicine transfer device 5800 according to a fifth embodiment.
Figure 17:
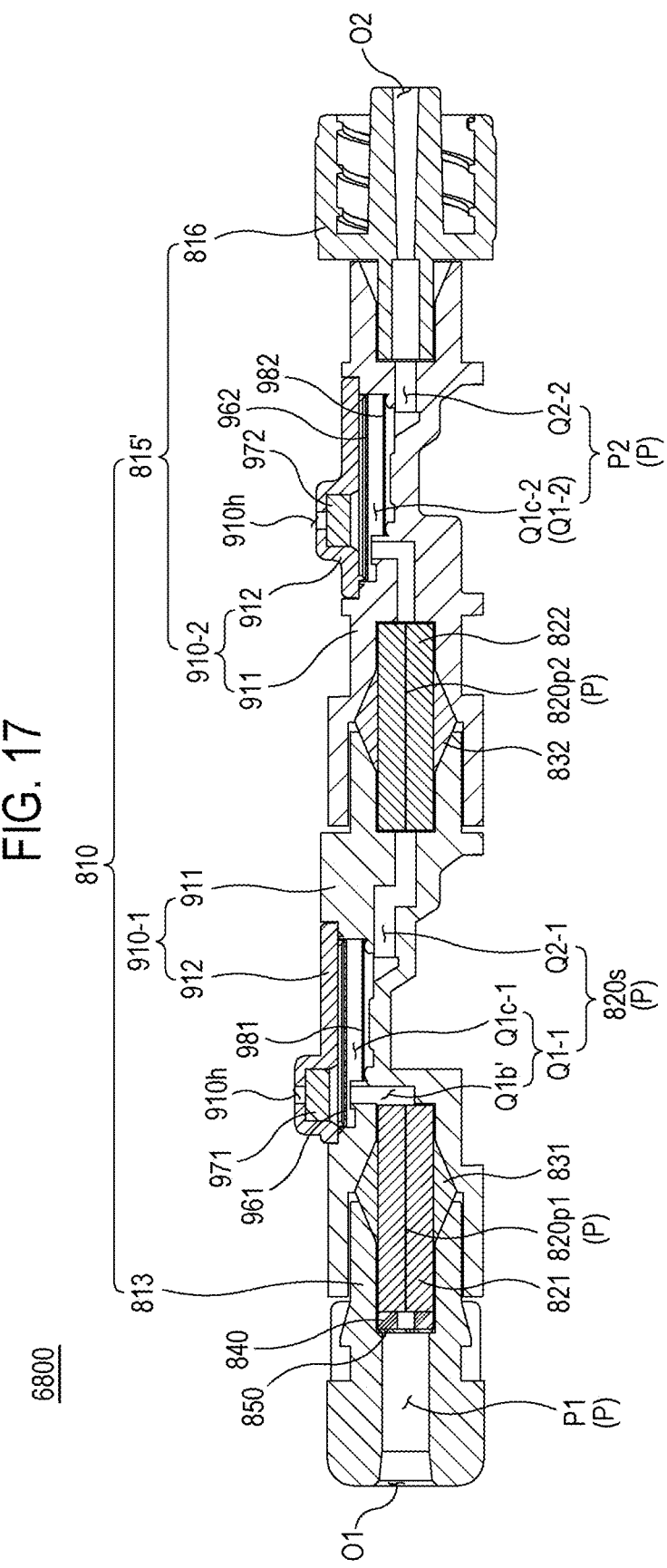
FIG. 17 is a vertical cross-sectional view of a filter-integrated medicine transfer device 6800 according to a sixth embodiment.
Figure 18:
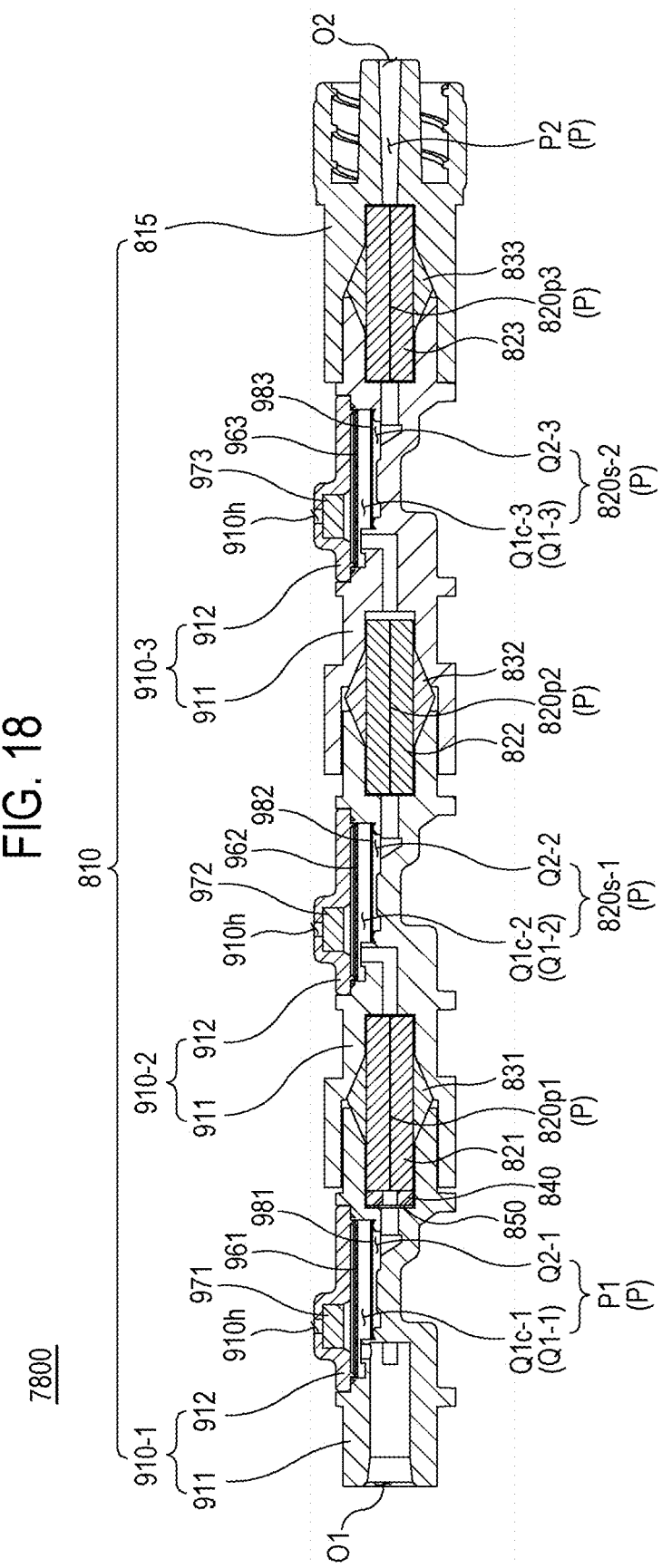
FIG. 18 is a vertical cross-sectional view of a filter-integrated medicine transfer device 7800 according to a seventh embodiment.

FIG. 14 is a vertical cross-sectional view of a filter-integrated medicine transfer device 3800 according to a third embodiment. FIG. 15 is a vertical cross-sectional view of a filter-integrated medicine transfer device 4800 according to a fourth embodiment. FIG. 16 is a vertical cross-sectional view of a filter-integrated medicine transfer device 5800 according to a fifth embodiment. FIG. 17 is a vertical cross-sectional view of a filter-integrated medicine transfer device 6800 according to a sixth embodiment. FIG. 18 is a vertical cross-sectional view of a filter-integrated medicine transfer device 7800 according to a seventh embodiment.

Referring to FIGS. 14 to 18, the contact channel $Q1c$ is positioned at a downstream side of the capillary channel (820p1 and/or 820p2) such that the medicinal liquid that has passed through the capillary channel (820p1 and/or 820p2) flows into the contact channel $Q1c$. Accordingly, it is possible to smoothly remove air produced in the capillary channel (820p1 and/or 820p2).

The medicine transfer device includes at least one medicine transfer pipe 820 and at least one air-passing filter 960. The medicine transfer pipe 820 may be disposed at the downstream side and/or the upstream side of the air-passing filter 960.

The at least one air-passing filter 960 may include a plurality of air-passing filters 960. For example, the at least one air-passing filter 960 may include n air-passing filters 960. An n-th air-passing filter means an air-passing filter disposed at the n-th position from the upstream side to the downstream side. An n-th contact channel $Q1c$ means a contact channel $Q1c$ disposed at the n-th position from the upstream side to the downstream side. n is a natural number.

The at least one medicine transfer pipe 820 may include a plurality of medicine transfer pipes 820. For example, the at least one medicine transfer pipe 820 may include n medicine transfer pipes 820. An n-th medicine transfer pipe means a medicine transfer pipe disposed at the n-th position from the upstream side to the downstream side. An n-th capillary channel 820p means a capillary channel 820p disposed at the n-th position from the upstream side to the downstream side. n is a natural number.

A medicine transfer pipe may be disposed at the downstream side of the n-th air-passing filter. A medicine transfer pipe may be disposed at the upstream side of the n-th air-passing filter. A medicine transfer pipe may be disposed at each of the upstream side and the downstream side of the n-th air-passing filter.

The contact channel $Q1c$ may be disposed at the downstream side of the n-th capillary channel 820p. The contact channel $Q1c$ may be disposed at the upstream side of the n-th capillary channel 820p. The contact channel $Q1c$ may be disposed at each of the upstream side and the downstream side of the n-th capillary channel 820p.

Referring to FIG. 14, in the medicine transfer device 3800 according to the third embodiment, the air-passing filter 960 is disposed at the downstream side of the first medicine transfer pipe 821 and the upstream side of the second medicine transfer pipe 822. The filter housing 910 of the medicine transfer device 3800 may also perform a function of a medicine transfer pipe housing. The intervention space 820s includes a first channel Q1 and a second channel Q2 divided by the boundary filter 980.

The housing 810 of the medicine transfer device 3800 may include an upstream housing part 813 coupled to the upstream side portion of the filter housing 910. The housing 810 of the medicine transfer device 3800 may include a downstream housing part 815 coupled to the downstream side portion of the filter housing 910.

The contact channel $Q1c$ of the medicine transfer device 3800 is positioned at the downstream side of the first capillary channel 820p1. The contact channel $Q1c$ of the medicine transfer device 3800 is positioned at the upstream side of the second capillary channel 820p2. The contact channel $Q1c$ constitutes a portion of the intervention space 820s. Accordingly, it is possible to collect air produced in the first capillary channel 820p1 or air that has passed through the first capillary channel 820p1 in the intervention space 820s, and then discharge the air to the outside.

Referring to FIG. 15, in the medicine transfer device 4800 according to the fourth embodiment, the air-passing filter 960 is disposed at the downstream side of the second medicine transfer pipe 822. The medicine transfer device 4800 includes a downstream housing part 815' coupled to the medicine transfer pipe housing 811. The downstream housing part 815' may include a filter housing 910. The downstream housing part 815' may further include an auxiliary housing part 816 coupled to the downstream side of the filter housing 910 and forming the discharge port O2. The downstream channel P2 includes a first channel Q1 and a second channel Q2 divided by the boundary filter 980. The housing 810 may include an upstream housing part 813 coupled to the upstream side portion of the medicine transfer pipe housing 811. The contact channel $Q1c$ of the medicine transfer device 4800 is positioned at the downstream side of the second capillary channel 820p2.

Referring to FIG. 16, in the medicine transfer device 5800 according to the fifth embodiment, the first air-passing filter 961 is disposed at the upstream side of the first medicine transfer pipe 821. The second air-passing filter 962 of the medicine transfer device 5800 is disposed at the downstream side of the first medicine transfer pipe 821 and the upstream side of the second medicine transfer pipe 822. The medicine transfer device 5800 may include a secondary air-passing filter 971 and a first boundary filter 981, corresponding to the first air-passing filter 961. The medicine transfer device 5800 may include a secondary air-passing filter 972 and a second boundary filter 982, corresponding to the second air-passing filter 962. A first filter housing 910-1 in which the first air-passing filter 961 is disposed may be referred to as an upstream housing 910-1. A second filter housing 910-2 in which the second air-passing filter 962 is disposed may be referred to as a medicine transfer pipe housing 910-2. The upstream channel P1 includes a first channel Q1-1 and a second channel Q2-1 divided by the first boundary filter 981. The intervention space 820s includes a first channel Q1-1 and a second channel Q2-1 divided by the second boundary filter 982.

A first contact channel $Q1c$-1 of the medicine transfer device 5800 is positioned at the upstream side of the first capillary channel 820p1. A second contact channel $Q1c$-2 of the medicine transfer device 5800 is positioned at the downstream side of the first capillary channel 820p1. The second contact channel $Q1c$-2 of the medicine transfer device 5800 is positioned at the upstream side of the second capillary channel 820p2. The second contact channel $Q1c$-2 constitutes a portion of the intervention space 820s.

Referring to FIG. 17, in the medicine transfer device 6800 according to the sixth embodiment, the first air-passing filter 961 is disposed at the downstream side of the first medicine transfer pipe 821 and the upstream side of the second medicine transfer pipe 822. The second air-passing filter 962 of the medicine transfer device 6800 is disposed at the downstream side of the second medicine transfer pipe 822. The medicine transfer device 6800 may include a secondary air-passing filter 971 and a first boundary filter 981, corresponding to the first air-passing filter 961. The medicine transfer device 8800 may include a secondary air-passing filter 972 and a second boundary filter 982, corresponding to the second air-passing filter 962. A first filter housing 910-1 in which the first air-passing filter 961 is disposed may be referred to as a medicine transfer pipe housing 910-1. A downstream housing part 815' of the medicine transfer device 6800 includes a second filer housing 910-2 in which the second air-passing filter 962 is disposed. The downstream housing part 815' may further include an auxiliary housing part 816 coupled to the downstream side of the second filter housing 910-2 and forming the discharge port O2. The intervention space 820s includes a first channel Q1-1 and a second channel Q2-1 divided by the first boundary filter 981. The downstream channel P2 includes a first channel Q1-2 and a second channel Q2-2 divided by the second boundary filter 982.

A first contact channel Q1c-1 of the medicine transfer device 6800 is positioned at the downstream side of the first capillary channel 820p1. The first contact channel Q1c-1 of the medicine transfer device 6800 is positioned at the upstream side of the second capillary channel 820p2. The first contact channel Q1c-1 constitutes a portion of the intervention space 820s. A second contact channel Q1c-2 of the medicine transfer device 6800 is positioned at the downstream side of the second capillary channel 820p2.

In the medicine transfer device 6800, a facing channel Q1b' may be directly connected to a downstream end of the capillary channel 820p1. That is, an upstream end of the facing channel Q1b' may be directly connected to the downstream end of the capillary channel 820p1 without the intake channel described above. By disposing the facing channel Q1b' closer to the outlet of the capillary channel 820p1, it is possible to quickly discharge air discharged from the capillary channel 820p1 to the outside through the air-passing filter 961. An outlet of the facing channel Q1b' may be disposed to face the air-passing filter 961. The outlet of the facing channel Q1b' may be disposed to face the secondary air-passing filter 971. The outlet of the facing channel Q1b' means the joint of the facing channel Q1b' and the contact channel Q1c-1.

Referring to FIG. 18, the medicine transfer device 7800 according to the seventh embodiment further includes a third medicine transfer pipe 823 having a third capillary channel 820p3 disposed at the downstream side of the second capillary channel 820p2 such that a medicinal liquid that has passed through the second capillary channel 820p2 flows therein. The medicine transfer device 7800 further includes a third sealing member 833 corresponding to the third medicine transfer pipe 823. The medicine transfer device 7800 includes a third air-passing filter 963. The medicine transfer device 7800 may include a secondary air-passing filter 973 and a third boundary filter 983, corresponding to the third air-passing filter 963. In the medicine transfer device 7800, the first air-passing filter 971, the first medicine transfer pipe 821, the second air-passing filter 972, the second medicine transfer pipe 822, the third air-passing filter 973, and the third medicine transfer pipe 823 are sequentially disposed.

A first intervention space 820s-1 is positioned between the first medicine transfer pipe 821 and the second medicine transfer pipe 822 in the housing 810 of the medicine transfer device 7800. A second intervention space 820s-2 is positioned between the second medicine transfer pipe 822 and the third medicine transfer pipe 823 in the housing 810. The second capillary channel 820p2, the second intervention space 820s-2, and the third capillary channel 820p3 are sequentially positioned on the channel P. That is, a channel cross-sectional area of the second intervention space 820s-2 is larger than a channel cross-sectional area of the second capillary channel 820p2 and a channel cross-sectional area of the third capillary channel 820p3. The second intervention space 820s-2 may be referred to as an additional intervention space 820s-2.

The housing 810 of the medicine transfer device 7800 includes a first filter housing 910-1 in which the first air-passing filter 961 is disposed, a second filter housing 910-2 in which the second air-passing filter 962 is disposed, and a third filter housing 910-3 in which the third air-passing filter 963 is disposed. The upstream channel P1 includes a first channel Q1-1 and a second channel Q2-1 divided by the first boundary filter 981. The first intervention space 820s-1 includes a first channel Q1-2 and a second channel Q2-2 divided by the second boundary filter 982. The second intervention space 820s-2 includes a first channel Q1-3 and a second channel Q2-3 divided by the third boundary filter 983.

A first contact channel Q1c-1 of the medicine transfer device 7800 is positioned at the upstream side of the first capillary channel 820p1. A second contact channel Q1c-2 of the medicine transfer device 7800 is positioned at the downstream side of the first capillary channel 820p1 and at the upstream side of the second capillary channel 820p-2. The second contact channel Q1c-2 constitutes a portion of a first intervention space 820s-1. A third contact channel Q1c-3 of the medicine transfer device 7800 is positioned at the downstream side of the second capillary channel 820p2 and at the upstream side of the third capillary channel 820p. The third contact channel Q1c-3 constitutes a portion of a second intervention space 820s-2.

Although the spirit of the present disclosure has been described with reference to the embodiments and the examples shown in the figures, it should be understood that the present disclosure can be replaced, changed, and modified by those skilled in the art in various ways without departing from the spirit and scope of the present disclosure. Further, those replacements, changes, and modifications should be considered as being included in the claims.

The invention claimed is:
1. A filter-integrated medicine transfer device in which a medicinal liquid channel is formed, comprising:
  a housing having an air passage that diverges from the medicinal liquid channel and is connected to outside;
  at least one hydrophobic air-passing filter disposed in the housing and disposed at a boundary between the air passage and the medicinal liquid channel; and
  at least one medicine transfer pipe disposed in the housing,
  wherein the at least one medicine transfer pipe includes:
    a first medicine transfer pipe having a first capillary channel constituting a portion of the medicinal liquid channel; and
    a second medicine transfer pipe having a second capillary channel disposed at a downstream side of the first capillary channel such that a medicinal liquid that has passed through the first capillary channel flows into the second capillary channel.

2. The filter-integrated medicine transfer device of claim 1, wherein the hydrophobic air-passing filter is configured to pass air in a first direction that is any one direction crossing an extension direction of at least one capillary channel of the first capillary channel or the second capillary channel.

3. The filter-integrated medicine transfer device of claim 2, wherein the housing has a vent hole positioned at a position where the air passage is connected to an external space, and being open in the first direction.

4. The filter-integrated medicine transfer device of claim 1, wherein the housing includes:
a medicine transfer pipe housing to which the medicine transfer pipe is coupled; and
a filter housing to which the hydrophobic air-passing filter is coupled,
the medicinal liquid channel includes a filtering channel formed in the filter housing, and
the filtering channel has at least one curved or bent portion.

5. The filter-integrated medicine transfer device of claim 4, wherein the at least one curved or bent portion is curved or bent in a first direction crossing an extension direction of at least one capillary channel of the first capillary channel or the second capillary channel.

6. The filter-integrated medicine transfer device of claim 1, wherein the medicinal liquid channel includes a contact channel configured such that the medicinal liquid in the contact channel comes in contact with the hydrophobic air-passing filter, and
the contact channel is positioned at an upstream side or a downstream side of at least one capillary channel of the first capillary channel or the second capillary channel.

7. The filter-integrated medicine transfer device of claim 6, wherein the contact channel is positioned at an upstream side of the at least one capillary channel such that the medicinal liquid that has passed through the contact channel flows into the at least one capillary channel.

8. The filter-integrated medicine transfer device of claim 6, wherein the contact channel is positioned at a downstream side of the at least one capillary channel such that the medicinal liquid that has passed through the at least one capillary channel flows into the contact channel.

9. The filter-integrated medicine transfer device of claim 1, wherein the medicinal liquid channel includes a contact channel configured such that the medicinal liquid in the contact channel comes in contact with the hydrophobic air-passing filter, and
the contact channel is positioned at a downstream side of the first capillary channel and at an upstream side of the second capillary channel.

10. The filter-integrated medicine transfer device of claim 1, further comprising a hydrophilic boundary filter disposed at a boundary between a first channel at an upstream side in the medicinal liquid channel and a second channel at a downstream side in the medicinal liquid channel,
wherein the hydrophobic air-passing filter is disposed at a boundary between the air passage and the first channel.

11. The filter-integrated medicine transfer device of claim 10, wherein at least one capillary channel of the first capillary channel or the second capillary channel is positioned at a downstream side of the second channel.

12. The filter-integrated medicine transfer device of claim 10, further comprising an intake filter disposed at an upstream side of at least one capillary channel of the first capillary channel or the second capillary channel and a downstream side of the boundary filter to pass the medicinal liquid.

13. The filter-integrated medicine transfer device of claim 1, further comprising an additional hydrophobic air-passing filter disposed in the air passage and configured to pass air that has passed through the hydrophobic air-passing filter.

14. A medicinal liquid injection apparatus comprising:
a pump configured to press a medicinal liquid;
an extension tube in which the medicinal liquid flowing out of the pump flows by pressure applied by the pump; and
a filter-integrated medicine transfer device connected to the extension tube and having a medicinal liquid channel,
wherein the filter-integrated medicine transfer device includes:
a housing having an air passage that diverges from the medicinal liquid channel and is connected to outside;
at least one hydrophobic air-passing filter disposed in the housing and disposed at a boundary between the air passage and the medicinal liquid channel; and
at least one medicine transfer pipe disposed in the housing,
wherein the at least one medicine transfer pipe includes:
a first medicine transfer pipe having a first capillary channel constituting a portion of the medicinal liquid channel; and
a second medicine transfer pipe having a second capillary channel disposed at a downstream side of the first capillary channel such that the medicinal liquid that has passed through the first capillary channel flows into the second capillary channel.

* * * * *